(12) United States Patent
Gera et al.

(10) Patent No.: US 11,896,445 B2
(45) Date of Patent: Feb. 13, 2024

(54) ILIAC PIN AND ADAPTER

(71) Applicant: AUGMEDICS LTD., Yokneam Illit (IL)

(72) Inventors: Tomer Gera, Kfar Tavor (IL); Daniel Horovitz, Kfar Tavor (IL)

(73) Assignee: AUGMEDICS LTD., Yokneam Illit (IL)

( * ) Notice: Subject to any disclaimer, the term of this patent is extended or adjusted under 35 U.S.C. 154(b) by 127 days.

(21) Appl. No.: 17/368,859

(22) Filed: Jul. 7, 2021

(65) Prior Publication Data
US 2023/0009793 A1      Jan. 12, 2023

(51) Int. Cl.
    *A61B 90/00*          (2016.01)
(52) U.S. Cl.
    CPC .............. *A61B 90/39* (2016.02); *A61B 90/37* (2016.02); *A61B 2090/365* (2016.02); *A61B 2090/3916* (2016.02); *A61B 2090/3983* (2016.02); *A61B 2090/3991* (2016.02)
(58) Field of Classification Search
    CPC ................................ A61B 90/37; A61B 90/39
    See application file for complete search history.

(56) References Cited

U.S. PATENT DOCUMENTS

| | | |
|---|---|---|
| 3,690,776 A | 9/1972 | Zaporoshan |
| 4,459,358 A | 7/1984 | Berke |
| 4,711,512 A | 12/1987 | Upatnieks |
| 4,863,238 A | 9/1989 | Brewster |
| 4,944,739 A | 7/1990 | Torre |
| 5,441,042 A | 8/1995 | Putman |
| 5,442,146 A | 8/1995 | Bell et al. |
| 5,510,832 A | 4/1996 | Garcia |
| D370,309 S  | 5/1996 | Stucky |
| 5,636,255 A | 6/1997 | Ellis |
| 5,665,092 A | 9/1997 | Mangiardi et al. |
| 5,771,121 A | 6/1998 | Hentschke |
| 5,792,046 A | 8/1998 | Dobrovolny |

(Continued)

FOREIGN PATENT DOCUMENTS

| | | |
|---|---|---|
| CA | 3022448 A1 | 2/2018 |
| CA | 3034314 A1 | 2/2018 |

(Continued)

OTHER PUBLICATIONS

International Application # PCT/IB2022/056212 Search Report dated Oct. 3, 2022.

(Continued)

*Primary Examiner* — Sameh R Boles
(74) *Attorney, Agent, or Firm* — KNOBBE, MARTENS, OLSON & BEAR, LLP

(57) ABSTRACT

Apparatus for mounting in a bone of a patient, consisting of a rigid elongated member having an axis of symmetry and a distal section, a proximal section, and an intermediate section connecting the distal and proximal sections. The apparatus has n helical blades, formed in the distal section, distributed symmetrically about the axis, each of the blades having a helix angle greater than zero and less than 45°. A cross-section of the distal section, taken orthogonally to the axis of symmetry, includes n mirror planes containing the axis of symmetry, wherein n is a whole number greater than one, and wherein the blades are configured to penetrate into the bone and engage stably therein. Adapters coupling the apparatus to different types of markers are also described.

10 Claims, 12 Drawing Sheets

(56) References Cited

U.S. PATENT DOCUMENTS

| | | |
|---|---|---|
| 5,841,507 A | 11/1998 | Barnes |
| 6,006,126 A | 12/1999 | Cosman |
| 6,038,467 A | 3/2000 | De Bliek et al. |
| 6,125,164 A | 9/2000 | Murphy et al. |
| 6,147,805 A | 11/2000 | Fergason |
| 6,227,667 B1 | 5/2001 | Halldorsson et al. |
| 6,256,529 B1 | 7/2001 | Holupka et al. |
| 6,285,505 B1 | 9/2001 | Melville et al. |
| 6,314,310 B1 | 11/2001 | Ben-Haim et al. |
| 6,349,001 B1 | 2/2002 | Spitzer |
| 6,444,192 B1 | 9/2002 | Mattrey |
| 6,447,503 B1 | 9/2002 | Wynne et al. |
| 6,449,090 B1 | 9/2002 | Omar et al. |
| 6,456,405 B2 | 9/2002 | Horikoshi et al. |
| 6,456,868 B2 | 9/2002 | Saito et al. |
| 6,474,159 B1 | 11/2002 | Foxlin et al. |
| 6,518,939 B1 | 2/2003 | Kikuchi |
| 6,527,777 B2 | 3/2003 | Justin |
| 6,529,331 B2 | 3/2003 | Massof et al. |
| 6,549,645 B1 | 4/2003 | Oikawa et al. |
| 6,578,962 B1 | 6/2003 | Amir et al. |
| 6,609,022 B2 | 8/2003 | Vilsmeier et al. |
| 6,610,009 B2 | 8/2003 | Person |
| D480,476 S | 10/2003 | Martinson et al. |
| 6,659,611 B2 | 12/2003 | Amir et al. |
| 6,675,040 B1 | 1/2004 | Cosman |
| 6,683,584 B2 | 1/2004 | Ronzani et al. |
| 6,690,964 B2 | 2/2004 | Bieger et al. |
| 6,714,810 B2 | 3/2004 | Grzeszczuk et al. |
| 6,737,425 B1 | 5/2004 | Yamamoto et al. |
| 6,740,882 B2 | 5/2004 | Weinberg |
| 6,757,068 B2 | 6/2004 | Foxlin |
| 6,759,200 B1 | 7/2004 | Stanton, Jr. |
| 6,847,336 B1 | 1/2005 | Lemelson et al. |
| 6,856,324 B2 | 2/2005 | Sauer et al. |
| 6,856,826 B2 | 2/2005 | Seeley et al. |
| 6,891,518 B2 | 5/2005 | Sauer et al. |
| 6,900,777 B1 | 5/2005 | Hebert et al. |
| 6,919,867 B2 | 7/2005 | Sauer |
| 6,921,167 B2 | 7/2005 | Nagata |
| 6,966,668 B2 | 11/2005 | Cugini et al. |
| 6,980,849 B2 | 12/2005 | Sasso |
| 6,993,374 B2 | 1/2006 | Sasso |
| 6,997,552 B1 | 2/2006 | Hung |
| 6,999,239 B1 | 2/2006 | Martins et al. |
| 7,035,371 B2 | 4/2006 | Boese et al. |
| 7,043,961 B2 | 5/2006 | Pandey et al. |
| 7,103,233 B2 | 9/2006 | Stearns |
| 7,107,091 B2 | 9/2006 | Jutras et al. |
| 7,112,656 B2 | 9/2006 | Desnoyers et al. |
| 7,141,812 B2 | 11/2006 | Appleby et al. |
| 7,157,459 B2 | 1/2007 | Ohta et al. |
| 7,169,785 B2 | 1/2007 | Timmer et al. |
| 7,171,255 B2 | 1/2007 | Holupka et al. |
| 7,176,936 B2 | 2/2007 | Sauer et al. |
| 7,187,792 B2 | 3/2007 | Fu et al. |
| 7,190,331 B2 | 3/2007 | Genc et al. |
| 7,194,295 B2 | 3/2007 | Vilsmeier |
| 7,215,322 B2 | 5/2007 | Genc et al. |
| 7,229,078 B2 | 6/2007 | Lechot |
| 7,231,076 B2 | 6/2007 | Fu et al. |
| 7,235,076 B2 | 6/2007 | Pacheco |
| 7,239,330 B2 | 7/2007 | Sauer et al. |
| 7,259,266 B2 | 8/2007 | Carter et al. |
| 7,260,426 B2 | 8/2007 | Schweikard et al. |
| 7,269,192 B2 | 9/2007 | Hayashi |
| 7,281,826 B2 | 10/2007 | Huang |
| 7,320,556 B2 | 1/2008 | Vagn-Erik |
| 7,330,578 B2 | 2/2008 | Wang et al. |
| 7,359,535 B2 | 4/2008 | Salla et al. |
| 7,364,314 B2 | 4/2008 | Nilsen et al. |
| 7,366,934 B1 | 4/2008 | Narayan et al. |
| 7,379,077 B2 | 5/2008 | Bani-Hashemi et al. |
| 7,431,453 B2 | 10/2008 | Hogan |
| 7,435,219 B2 | 10/2008 | Kim |
| 7,458,977 B2 | 12/2008 | Mcginley et al. |
| 7,462,852 B2 | 12/2008 | Appleby et al. |
| 7,493,153 B2 | 2/2009 | Ahmed et al. |
| 7,505,617 B2 | 3/2009 | Fu et al. |
| 7,507,968 B2 | 3/2009 | Wollenweber et al. |
| 7,518,136 B2 | 4/2009 | Appleby et al. |
| 7,525,735 B2 | 4/2009 | Sottilare et al. |
| D592,691 S | 5/2009 | Chang |
| D592,692 S | 5/2009 | Chang |
| D592,693 S | 5/2009 | Chang |
| 7,536,216 B2 | 5/2009 | Geiger et al. |
| 7,542,791 B2 | 6/2009 | Mire et al. |
| 7,556,428 B2 | 7/2009 | Sukovic et al. |
| 7,557,824 B2 | 7/2009 | Holliman |
| 7,563,228 B2 | 7/2009 | Ma et al. |
| 7,567,834 B2 | 7/2009 | Clayton et al. |
| 7,586,686 B1 | 9/2009 | Hall |
| D602,620 S | 10/2009 | Cristoforo |
| 7,605,826 B2 | 10/2009 | Sauer |
| 7,606,613 B2 | 10/2009 | Simon et al. |
| 7,607,775 B2 | 10/2009 | Hermanson et al. |
| 7,620,223 B2 | 11/2009 | Xu et al. |
| 7,627,085 B2 | 12/2009 | Boyden et al. |
| 7,630,753 B2 | 12/2009 | Simon et al. |
| 7,633,501 B2 | 12/2009 | Wood et al. |
| 7,645,050 B2 | 1/2010 | Wilt et al. |
| 7,653,226 B2 | 1/2010 | Guhring et al. |
| 7,689,019 B2 | 3/2010 | Boese et al. |
| 7,689,042 B2 | 3/2010 | Brunner et al. |
| 7,689,320 B2 | 3/2010 | Prisco et al. |
| 7,699,486 B1 | 4/2010 | Beiner |
| 7,699,793 B2 | 4/2010 | Goette et al. |
| 7,719,769 B2 | 5/2010 | Sugihara et al. |
| D617,825 S | 6/2010 | Chang |
| 7,734,327 B2 | 6/2010 | Colquhoun |
| D619,285 S | 7/2010 | Cristoforo |
| 7,751,865 B2 | 7/2010 | Jascob et al. |
| 7,758,204 B2 | 7/2010 | Klipstein et al. |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |
| 7,831,096 B2 | 11/2010 | Williamson, Jr. |
| 7,835,778 B2 | 11/2010 | Foley et al. |
| 7,835,784 B2 | 11/2010 | Mire et al. |
| 7,837,987 B2 | 11/2010 | Shi et al. |
| 7,840,093 B2 | 11/2010 | Fu et al. |
| 7,840,253 B2 | 11/2010 | Tremblay et al. |
| 7,840,256 B2 | 11/2010 | Lakin et al. |
| 7,853,305 B2 | 12/2010 | Simon et al. |
| 7,854,705 B2 | 12/2010 | Pawluczyk et al. |
| 7,857,271 B2 | 12/2010 | Lees |
| 7,860,282 B2 | 12/2010 | Boese et al. |
| D630,766 S | 1/2011 | Harbin |
| 7,865,269 B2 | 1/2011 | Prisco et al. |
| 7,874,686 B2 | 1/2011 | Rossner et al. |
| 7,881,770 B2 | 2/2011 | Melkent et al. |
| 7,893,413 B1 | 2/2011 | Appleby et al. |
| 7,894,649 B2 | 2/2011 | Fu et al. |
| 7,920,162 B2 | 4/2011 | Masini et al. |
| 7,938,553 B1 | 5/2011 | Beiner |
| 7,945,310 B2 | 5/2011 | Gattani et al. |
| 7,953,471 B2 | 5/2011 | Clayton et al. |
| 7,969,383 B2 | 6/2011 | Eberl et al. |
| 7,974,677 B2 | 7/2011 | Mire et al. |
| 7,985,756 B2 | 7/2011 | Barlow et al. |
| 7,991,557 B2 | 8/2011 | Liew et al. |
| 7,993,353 B2 | 8/2011 | Roner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong et al. |
| 8,045,266 B2 | 10/2011 | Nakamura |
| 8,060,181 B2 | 11/2011 | Rodriguez et al. |
| 8,068,581 B2 | 11/2011 | Boese et al. |
| 8,068,896 B2 | 11/2011 | Daghighian et al. |

(56) References Cited

U.S. PATENT DOCUMENTS

| | | | |
|---|---|---|---|
| 8,077,943 | B2 | 12/2011 | Williams et al. |
| 8,079,957 | B2 | 12/2011 | Ma et al. |
| 8,085,075 | B2 | 12/2011 | Huffman et al. |
| 8,085,897 | B2 | 12/2011 | Morton |
| 8,090,175 | B2 | 1/2012 | Fu et al. |
| 8,092,400 | B2 | 1/2012 | Warkentine et al. |
| 8,108,072 | B2 | 1/2012 | Zhao et al. |
| 8,112,292 | B2 | 2/2012 | Simon |
| 8,116,847 | B2 | 2/2012 | Gattani et al. |
| 8,120,847 | B2 | 2/2012 | Chang |
| 8,121,255 | B2 | 2/2012 | Sugiyama |
| 8,155,479 | B2 | 4/2012 | Hoffman et al. |
| 8,180,429 | B2 | 5/2012 | Sasso |
| 8,208,599 | B2 | 6/2012 | Ye et al. |
| 8,216,211 | B2 | 7/2012 | Mathis et al. |
| 8,221,402 | B2 | 7/2012 | Francischelli et al. |
| 8,239,001 | B2 | 8/2012 | Verard et al. |
| 8,244,012 | B2 | 8/2012 | Liang et al. |
| 8,253,778 | B2 | 8/2012 | Atsushi |
| 8,271,069 | B2 | 9/2012 | Jascob et al. |
| 8,280,491 | B2 | 10/2012 | Kuduvalli et al. |
| 8,285,021 | B2 | 10/2012 | Boese et al. |
| 8,300,315 | B2 | 10/2012 | Kobayashi |
| 8,305,685 | B2 | 11/2012 | Heine et al. |
| 8,306,305 | B2 | 11/2012 | Porat et al. |
| 8,309,932 | B2 | 11/2012 | Haselman et al. |
| 8,317,320 | B2 | 11/2012 | Huang |
| 8,328,815 | B2 | 12/2012 | Farr et al. |
| 8,335,553 | B2 | 12/2012 | Rubner et al. |
| 8,335,557 | B2 | 12/2012 | Maschke |
| 8,340,379 | B2 | 12/2012 | Razzaque et al. |
| 8,369,925 | B2 | 2/2013 | Giesel et al. |
| 8,386,022 | B2 | 2/2013 | Jutras et al. |
| 8,394,144 | B2 | 3/2013 | Zehavi et al. |
| 8,398,541 | B2 | 3/2013 | Dimaio et al. |
| 8,444,266 | B2 | 5/2013 | Waters |
| 8,457,719 | B2 | 6/2013 | Moctezuma De La Barrera et al. |
| 8,467,851 | B2 | 6/2013 | Mire et al. |
| 8,469,902 | B2 | 6/2013 | Dick et al. |
| 8,494,612 | B2 | 7/2013 | Vetter et al. |
| 8,509,503 | B2 | 8/2013 | Nahum et al. |
| 8,511,827 | B2 | 8/2013 | Hua et al. |
| 8,531,394 | B2 | 9/2013 | Maltz |
| 8,540,364 | B2 | 9/2013 | Waters |
| 8,545,012 | B2 | 10/2013 | Waters |
| 8,548,567 | B2 | 10/2013 | Maschke et al. |
| 8,556,883 | B2 | 10/2013 | Saleh |
| 8,559,596 | B2 | 10/2013 | Thomson et al. |
| 8,567,945 | B2 | 10/2013 | Waters |
| 8,571,353 | B2 | 10/2013 | Watanabe |
| 8,585,598 | B2 | 11/2013 | Razzaque et al. |
| 8,600,001 | B2 | 12/2013 | Schweizer |
| 8,600,477 | B2 | 12/2013 | Beyar et al. |
| 8,605,199 | B2 | 12/2013 | Imai |
| 8,611,988 | B2 | 12/2013 | Miyamoto |
| 8,612,024 | B2 | 12/2013 | Stone et al. |
| 8,634,897 | B2 | 1/2014 | Simon et al. |
| 8,641,621 | B2 | 2/2014 | Razzaque et al. |
| 8,643,950 | B2 | 2/2014 | König |
| 8,644,907 | B2 | 2/2014 | Hartmann et al. |
| 8,674,902 | B2 | 3/2014 | Park et al. |
| 8,686,923 | B2 | 4/2014 | Eberl et al. |
| 8,690,581 | B2 | 4/2014 | Ruf et al. |
| 8,690,776 | B2 | 4/2014 | Razzaque et al. |
| 8,692,845 | B2 | 4/2014 | Fedorovskaya et al. |
| 8,693,632 | B2 | 4/2014 | Allison |
| 8,694,075 | B2 | 4/2014 | Groszmann et al. |
| 8,699,765 | B2 | 4/2014 | Hao et al. |
| 8,705,829 | B2 | 4/2014 | Frank et al. |
| 8,737,708 | B2 | 5/2014 | Hartmann et al. |
| 8,746,887 | B2 | 6/2014 | Shestak et al. |
| 8,784,450 | B2 | 7/2014 | Moskowitz et al. |
| 8,786,689 | B1 | 7/2014 | Liu |
| D710,545 | S | 8/2014 | Wu |
| D710,546 | S | 8/2014 | Wu |
| 8,827,934 | B2 | 9/2014 | Chopra et al. |
| 8,831,706 | B2 | 9/2014 | Fu et al. |
| 8,838,199 | B2 | 9/2014 | Simon et al. |
| 8,848,977 | B2 | 9/2014 | Bammer et al. |
| 8,855,395 | B2 | 10/2014 | Baturin et al. |
| 8,878,900 | B2 | 11/2014 | Yang et al. |
| 8,885,177 | B2 | 11/2014 | Ben-Yishai et al. |
| 8,890,772 | B2 | 11/2014 | Woo et al. |
| 8,890,773 | B1 | 11/2014 | Pederson |
| 8,890,943 | B2 | 11/2014 | Lee et al. |
| 8,897,514 | B2 | 11/2014 | Feikas et al. |
| 8,900,131 | B2 | 12/2014 | Chopra et al. |
| 8,903,150 | B2 | 12/2014 | Star-Lack et al. |
| 8,908,952 | B2 | 12/2014 | Isaacs et al. |
| 8,911,358 | B2 | 12/2014 | Koninckx et al. |
| 8,917,268 | B2 | 12/2014 | Johnsen et al. |
| 8,920,776 | B2 | 12/2014 | Gaiger et al. |
| 8,922,589 | B2 | 12/2014 | Laor |
| 8,941,559 | B2 | 1/2015 | Bar-Zeev et al. |
| 8,942,455 | B2 | 1/2015 | Chou et al. |
| 8,950,877 | B2 | 2/2015 | Northey et al. |
| 8,953,246 | B2 | 2/2015 | Koenig |
| 8,965,583 | B2 | 2/2015 | Ortmaier et al. |
| 8,969,829 | B2 | 3/2015 | Wollenweber et al. |
| 8,989,349 | B2 | 3/2015 | Thomson et al. |
| 8,992,580 | B2 | 3/2015 | Bar et al. |
| 8,994,729 | B2 | 3/2015 | Nakamura |
| 8,994,795 | B2 | 3/2015 | Oh |
| 9,004,711 | B2 | 4/2015 | Gerolemou |
| 9,005,211 | B2 | 4/2015 | Brundobler et al. |
| 9,011,441 | B2 | 4/2015 | Bertagnoli et al. |
| 9,057,759 | B2 | 6/2015 | Klingenbeck et al. |
| 9,060,757 | B2 | 6/2015 | Lawson et al. |
| 9,066,751 | B2 | 6/2015 | Sasso |
| 9,081,436 | B1 | 7/2015 | Berme et al. |
| 9,084,635 | B2 | 7/2015 | Nuckley et al. |
| 9,085,643 | B2 | 7/2015 | Svanborg et al. |
| 9,087,471 | B2 | 7/2015 | Miao |
| 9,100,643 | B2 | 8/2015 | Mcdowall et al. |
| 9,101,394 | B2 | 8/2015 | Arata et al. |
| 9,111,175 | B2 | 8/2015 | Strommer et al. |
| 9,123,155 | B2 | 9/2015 | Cunningham et al. |
| 9,125,556 | B2 | 9/2015 | Zehavi et al. |
| 9,129,054 | B2 | 9/2015 | Nawana et al. |
| 9,129,372 | B2 | 9/2015 | Kriston et al. |
| 9,132,361 | B2 | 9/2015 | Smithwick |
| 9,141,873 | B2 | 9/2015 | Takemoto |
| 9,142,020 | B2 | 9/2015 | Deguise et al. |
| 9,149,317 | B2 | 10/2015 | Arthur et al. |
| 9,165,203 | B2 | 10/2015 | McCarthy |
| 9,179,984 | B2 | 11/2015 | Teichman et al. |
| D746,354 | S | 12/2015 | Chang |
| 9,208,916 | B2 | 12/2015 | Appleby et al. |
| 9,220,573 | B2 | 12/2015 | Kendrick et al. |
| 9,225,895 | B2 | 12/2015 | Kozinski |
| 9,232,982 | B2 | 1/2016 | Soler et al. |
| 9,235,934 | B2 | 1/2016 | Mandella et al. |
| 9,244,278 | B2 | 1/2016 | Sugiyama et al. |
| 9,247,240 | B2 | 1/2016 | Park et al. |
| 9,259,192 | B2 | 2/2016 | Ishihara |
| 9,265,572 | B2 | 2/2016 | Fuchs et al. |
| 9,269,192 | B2 | 2/2016 | Kobayashi |
| 9,283,052 | B2 | 3/2016 | Rodriguez Ponce |
| 9,286,730 | B2 | 3/2016 | Bar-Zeev et al. |
| 9,289,267 | B2 | 3/2016 | Sauer et al. |
| 9,300,949 | B2 | 3/2016 | Ahearn |
| 9,310,591 | B2 | 4/2016 | Hua et al. |
| 9,320,474 | B2 | 4/2016 | Demri et al. |
| 9,323,055 | B2 | 4/2016 | Baillot |
| 9,330,477 | B2 | 5/2016 | Rappel |
| 9,335,547 | B2 | 5/2016 | Takano et al. |
| 9,335,567 | B2 | 5/2016 | Nakamura |
| 9,341,704 | B2 | 5/2016 | Picard et al. |
| 9,344,686 | B2 | 5/2016 | Moharir |
| 9,349,066 | B2 | 5/2016 | Koo et al. |
| 9,349,520 | B2 | 5/2016 | Demetriou et al. |
| 9,364,294 | B2 | 6/2016 | Razzaque et al. |
| 9,370,332 | B2 | 6/2016 | Paladini et al. |
| 9,373,166 | B2 | 6/2016 | Azar |

(56) References Cited

U.S. PATENT DOCUMENTS

| | | |
|---|---|---|
| 9,375,639 B2 | 6/2016 | Kobayashi et al. |
| 9,378,558 B2 | 6/2016 | Kajiwara et al. |
| 9,380,287 B2 | 6/2016 | Nistico et al. |
| 9,387,008 B2 | 7/2016 | Sarvestani et al. |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko et al. |
| 9,424,611 B2 | 8/2016 | Kanjirathinkal et al. |
| 9,424,641 B2 | 8/2016 | Wiemker et al. |
| 9,438,894 B2 | 9/2016 | Park et al. |
| 9,443,488 B2 | 9/2016 | Borenstein et al. |
| 9,453,804 B2 | 9/2016 | Tahtali |
| 9,456,878 B2 | 10/2016 | Macfarlane et al. |
| 9,465,235 B2 | 10/2016 | Chang |
| 9,468,373 B2 | 10/2016 | Larsen |
| 9,470,908 B1 | 10/2016 | Frankel et al. |
| 9,473,766 B2 | 10/2016 | Douglas et al. |
| 9,492,222 B2 | 11/2016 | Singh |
| 9,495,585 B2 | 11/2016 | Bicer et al. |
| 9,498,132 B2 | 11/2016 | Maier-Hein et al. |
| 9,498,231 B2 | 11/2016 | Haider et al. |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme et al. |
| 9,530,382 B2 | 12/2016 | Simmons |
| 9,532,846 B2 | 1/2017 | Nakamura |
| 9,532,849 B2 | 1/2017 | Anderson et al. |
| 9,538,962 B1 | 1/2017 | Hannaford et al. |
| 9,545,233 B2 | 1/2017 | Sirpad et al. |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen et al. |
| 9,561,446 B2 | 2/2017 | Brecher |
| 9,565,415 B2 | 2/2017 | Zhang et al. |
| 9,572,661 B2 | 2/2017 | Robin et al. |
| 9,576,556 B2 | 2/2017 | Simmons |
| 9,581,822 B2 | 2/2017 | Morimoto |
| 9,612,657 B2 | 4/2017 | Bertram et al. |
| 9,629,595 B2 | 4/2017 | Walker et al. |
| 9,633,431 B2 | 4/2017 | Merlet |
| 9,645,395 B2 | 5/2017 | Bolas et al. |
| 9,646,423 B1 | 5/2017 | Sun et al. |
| 9,672,597 B2 | 6/2017 | Amiot et al. |
| 9,672,640 B2 | 6/2017 | Kleiner |
| 9,675,306 B2 | 6/2017 | Morton |
| 9,675,319 B1 | 6/2017 | Razzaque et al. |
| RE46,463 E | 7/2017 | Fienbloom et al. |
| 9,710,968 B2 | 7/2017 | Dillavou et al. |
| 9,713,502 B2 | 7/2017 | Finkman et al. |
| 9,724,119 B2 | 8/2017 | Hissong et al. |
| 9,724,165 B2 | 8/2017 | Arata et al. |
| 9,726,888 B2 | 8/2017 | Giartosio et al. |
| 9,728,006 B2 | 8/2017 | Varga |
| 9,729,831 B2 | 8/2017 | Birnkrant et al. |
| 9,757,034 B2 | 9/2017 | Desjardins et al. |
| 9,757,087 B2 | 9/2017 | Simon et al. |
| 9,766,441 B2 | 9/2017 | Rappel |
| 9,767,608 B2 | 9/2017 | Lee et al. |
| 9,770,203 B1 | 9/2017 | Berme et al. |
| 9,772,102 B1 | 9/2017 | Ferguson |
| 9,772,495 B2 | 9/2017 | Tam et al. |
| 9,791,138 B1 | 10/2017 | Feinbloom et al. |
| 9,800,995 B2 | 10/2017 | Libin et al. |
| 9,805,504 B2 | 10/2017 | Zhang et al. |
| 9,808,148 B2 | 11/2017 | Miller et al. |
| 9,839,448 B2 | 12/2017 | Reckling et al. |
| 9,844,413 B2 | 12/2017 | Daon et al. |
| 9,851,080 B2 | 12/2017 | Wilt et al. |
| 9,861,446 B2 | 1/2018 | Lang |
| 9,864,214 B2 | 1/2018 | Fass |
| 9,872,733 B2 | 1/2018 | Shoham et al. |
| 9,877,642 B2 | 1/2018 | Duret |
| 9,885,465 B2 | 2/2018 | Nguyen |
| 9,886,552 B2 | 2/2018 | Dillavou et al. |
| 9,892,564 B1 | 2/2018 | Cvetko et al. |
| 9,898,866 B2 | 2/2018 | Fuchs et al. |
| 9,901,414 B2 | 2/2018 | Lively et al. |
| 9,911,187 B2 | 3/2018 | Steinle et al. |
| 9,927,611 B2 | 3/2018 | Rudy et al. |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |
| 9,956,054 B2 | 5/2018 | Aguirre-Valencia |
| 9,958,674 B2 | 5/2018 | Border |
| 9,959,629 B2 | 5/2018 | Dillavou et al. |
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards et al. |
| 10,015,243 B2 | 7/2018 | Kazerani et al. |
| 10,016,243 B2 | 7/2018 | Esterberg |
| 10,022,064 B2 | 7/2018 | Kim et al. |
| 10,022,065 B2 | 7/2018 | Ben-Yishai et al. |
| 10,022,104 B2 | 7/2018 | Sell et al. |
| 10,023,615 B2 | 7/2018 | Bonny |
| 10,026,015 B2 | 7/2018 | Cavusoglu et al. |
| 10,034,713 B2 | 7/2018 | Yang et al. |
| 10,046,165 B2 | 8/2018 | Frewin et al. |
| 10,066,816 B2 | 9/2018 | Chang |
| 10,073,515 B2 | 9/2018 | Awdeh |
| 10,080,616 B2 | 9/2018 | Wilkinson et al. |
| 10,082,680 B2 | 9/2018 | Chung |
| 10,085,709 B2 | 10/2018 | Lavallee et al. |
| 10,105,187 B2 | 10/2018 | Corndorf et al. |
| 10,107,483 B2 | 10/2018 | Oren |
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom et al. |
| 10,134,166 B2 | 11/2018 | Benishti et al. |
| 10,134,194 B2 | 11/2018 | Kepner et al. |
| 10,139,652 B2 | 11/2018 | Windham |
| 10,139,920 B2 | 11/2018 | Isaacs et al. |
| 10,142,496 B1 | 11/2018 | Rao et al. |
| 10,151,928 B2 | 12/2018 | Ushakov |
| 10,154,239 B2 | 12/2018 | Casas |
| 10,159,530 B2 | 12/2018 | Lang |
| 10,166,079 B2 | 1/2019 | Mclachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi et al. |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman et al. |
| 10,207,315 B2 | 2/2019 | Appleby et al. |
| 10,230,719 B2 | 3/2019 | Vaughn et al. |
| 10,231,893 B2 | 3/2019 | Lei et al. |
| 10,235,606 B2 | 3/2019 | Miao et al. |
| 10,240,769 B1 | 3/2019 | Braganca et al. |
| 10,247,965 B2 | 4/2019 | Ton |
| 10,251,724 B2 | 4/2019 | Mclachlin et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,339,719 B2 | 7/2019 | Jagga et al. |
| 10,352,543 B1 | 7/2019 | Braganca et al. |

(56) References Cited

U.S. PATENT DOCUMENTS

| | | |
|---|---|---|
| 10,357,146 B2 | 7/2019 | Fiebel et al. |
| 10,357,574 B2 | 7/2019 | Hilderbrand et al. |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Abou Shousha |
| 10,398,514 B2 | 9/2019 | Ryan et al. |
| 10,405,927 B1 | 9/2019 | Lang |
| 10,419,655 B2 | 9/2019 | Sivan |
| 10,420,626 B2 | 9/2019 | Tokuda et al. |
| 10,420,813 B2 | 9/2019 | Newell-Rogers et al. |
| 10,424,115 B2 | 9/2019 | Ellerbrock |
| 10,426,554 B2 | 10/2019 | Siewerdsen et al. |
| 10,429,675 B2 | 10/2019 | Greget |
| 10,431,008 B2 | 10/2019 | Djajadiningrat et al. |
| 10,433,814 B2 | 10/2019 | Razzaque et al. |
| 10,434,335 B2 | 10/2019 | Takahashi et al. |
| 10,444,514 B2 | 10/2019 | Abou Shousha et al. |
| 10,447,947 B2 | 10/2019 | Liu |
| 10,448,003 B2 | 10/2019 | Grafenberg |
| 10,449,040 B2 | 10/2019 | Lashinski et al. |
| 10,453,187 B2 | 10/2019 | Peterson et al. |
| 10,463,434 B2 | 11/2019 | Siegler et al. |
| 10,465,892 B1 | 11/2019 | Feinbloom et al. |
| 10,466,487 B2 | 11/2019 | Blum et al. |
| 10,470,732 B2 | 11/2019 | Baumgart et al. |
| 10,473,314 B1 | 11/2019 | Braganca et al. |
| 10,485,989 B2 | 11/2019 | Jordan et al. |
| 10,488,663 B2 | 11/2019 | Choi |
| D869,772 S | 12/2019 | Gand |
| D870,977 S | 12/2019 | Berggren et al. |
| 10,499,997 B2 | 12/2019 | Weinstein et al. |
| 10,504,231 B2 | 12/2019 | Fiala |
| 10,507,066 B2 | 12/2019 | Dimaio et al. |
| 10,511,822 B2 | 12/2019 | Casas |
| 10,517,544 B2 | 12/2019 | Taguchi et al. |
| 10,537,395 B2 | 1/2020 | Perez |
| 10,540,780 B1 | 1/2020 | Cousins et al. |
| 10,543,485 B2 | 1/2020 | Ismagilov et al. |
| 10,546,423 B2 | 1/2020 | Jones et al. |
| 10,548,557 B2 | 2/2020 | Lim et al. |
| 10,555,775 B2 | 2/2020 | Hoffman et al. |
| 10,568,535 B2 | 2/2020 | Roberts et al. |
| 10,571,696 B2 | 2/2020 | Urey et al. |
| 10,571,716 B2 | 2/2020 | Chapiro |
| 10,573,087 B2 | 2/2020 | Gallop et al. |
| 10,577,630 B2 | 3/2020 | Zhang et al. |
| 10,586,400 B2 | 3/2020 | Douglas |
| 10,592,748 B1 | 3/2020 | Cousins et al. |
| 10,594,998 B1 | 3/2020 | Casas |
| 10,595,716 B2 | 3/2020 | Nazareth et al. |
| 10,601,950 B2 | 3/2020 | Devam et al. |
| 10,602,114 B2 | 3/2020 | Casas |
| 10,603,113 B2 | 3/2020 | Lang |
| 10,603,133 B2 | 3/2020 | Wang et al. |
| 10,606,085 B2 | 3/2020 | Toyama |
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,625,099 B2 | 4/2020 | Takahashi et al. |
| 10,626,473 B2 | 4/2020 | Mariani et al. |
| 10,631,905 B2 | 4/2020 | Asfora et al. |
| 10,631,907 B2 | 4/2020 | Zucker et al. |
| 10,634,331 B1 | 4/2020 | Feinbloom et al. |
| 10,634,921 B2 | 4/2020 | Blum et al. |
| 10,638,080 B2 | 4/2020 | Ovchinnikov et al. |
| 10,646,285 B2 | 5/2020 | Siemionow et al. |
| 10,650,513 B2 | 5/2020 | Penney et al. |
| 10,650,594 B2 | 5/2020 | Jones et al. |
| 10,652,525 B2 | 5/2020 | Woods |
| 10,653,495 B2 | 5/2020 | Gregerson et al. |
| 10,660,715 B2 | 5/2020 | Dozeman |
| 10,663,738 B2 | 5/2020 | Carlvik et al. |
| 10,682,112 B2 | 6/2020 | Pizaine et al. |
| 10,682,767 B2 | 6/2020 | Grafenberg et al. |
| 10,687,901 B2 | 6/2020 | Thomas |
| 10,691,397 B1 | 6/2020 | Clements |
| 10,702,713 B2 | 7/2020 | Mori et al. |
| 10,709,398 B2 | 7/2020 | Schweizer |
| 10,713,801 B2 | 7/2020 | Jordan et al. |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,747,315 B2 | 8/2020 | Tungare et al. |
| 10,777,094 B1 | 9/2020 | Rao et al. |
| 10,777,315 B2 | 9/2020 | Zehavi et al. |
| 10,781,482 B2 | 9/2020 | Gubatayao et al. |
| 10,792,110 B2 | 10/2020 | Leung et al. |
| 10,799,145 B2 | 10/2020 | West et al. |
| 10,799,296 B2 | 10/2020 | Lang |
| 10,799,316 B2 | 10/2020 | Sela et al. |
| 10,810,799 B2 | 10/2020 | Tepper et al. |
| 10,818,019 B2 | 10/2020 | Piat et al. |
| 10,818,101 B2 | 10/2020 | Gallop et al. |
| 10,818,199 B2 | 10/2020 | Buras et al. |
| 10,825,563 B2 | 11/2020 | Gibby et al. |
| 10,831,943 B2 | 11/2020 | Santarone et al. |
| 10,835,296 B2 | 11/2020 | Elimelech et al. |
| 10,838,206 B2 | 11/2020 | Fortin-Deschnes et al. |
| 10,839,629 B2 | 11/2020 | Jones et al. |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker et al. |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino et al. |
| 10,869,517 B1 | 12/2020 | Halpern |
| 10,869,727 B2 | 12/2020 | Yanof et al. |
| 10,872,472 B2 | 12/2020 | Watola et al. |
| 10,877,262 B1 | 12/2020 | Luxembourg |
| 10,877,296 B2 | 12/2020 | Lindsey et al. |
| 10,878,639 B2 | 12/2020 | Douglas et al. |
| 10,893,260 B2 | 1/2021 | Trail et al. |
| 10,895,742 B2 | 1/2021 | Schneider et al. |
| 10,895,743 B2 | 1/2021 | Dausmann |
| 10,895,906 B2 | 1/2021 | West et al. |
| 10,898,151 B2 | 1/2021 | Harding et al. |
| 10,921,595 B2 | 2/2021 | Rakshit et al. |
| 10,921,613 B2 | 2/2021 | Gupta et al. |
| 10,928,321 B2 | 2/2021 | Rawle |
| 10,928,638 B2 | 2/2021 | Ninan et al. |
| 10,935,815 B1 | 3/2021 | Cesar |
| 10,935,816 B2 | 3/2021 | Ban et al. |
| 10,936,537 B2 | 3/2021 | Huston |
| 10,939,973 B2 | 3/2021 | Dimaio et al. |
| 10,939,977 B2 | 3/2021 | Messinger et al. |
| 10,941,933 B2 | 3/2021 | Ferguson |
| 10,946,108 B2 | 3/2021 | Zhang et al. |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 10,966,768 B2 | 4/2021 | Poulos |
| 10,993,754 B2 | 5/2021 | Kuntz et al. |
| 11,000,335 B2 | 5/2021 | Dorman |
| 11,006,093 B1 | 5/2021 | Hegyi |
| 11,013,550 B2 | 5/2021 | Rioux et al. |
| 11,013,560 B2 | 5/2021 | Lang |
| 11,013,562 B2 | 5/2021 | Marti et al. |
| 11,013,573 B2 | 5/2021 | Chang |
| 11,013,900 B2 | 5/2021 | Malek et al. |
| 11,019,988 B2 | 6/2021 | Fiebel et al. |
| 11,027,027 B2 | 6/2021 | Manning et al. |

(56) References Cited

U.S. PATENT DOCUMENTS

| | | | |
|---|---|---|---|
| 11,029,147 B2 | 6/2021 | Abovitz et al. |
| 11,030,809 B2 | 6/2021 | Wang |
| 11,041,173 B2 | 6/2021 | Zhang et al. |
| 11,045,663 B2 | 6/2021 | Mori et al. |
| 11,049,293 B2 | 6/2021 | Chae et al. |
| 11,049,476 B2 | 6/2021 | Fuchs et al. |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,065,062 B2 | 7/2021 | Frushour et al. |
| 11,067,387 B2 | 7/2021 | Marell et al. |
| 11,071,497 B2 | 7/2021 | Hallack et al. |
| 11,079,596 B2 | 8/2021 | Hua et al. |
| 11,087,039 B2 | 8/2021 | Duff et al. |
| 11,090,019 B2 | 8/2021 | Siemionow et al. |
| 11,097,129 B2 | 8/2021 | Sakata et al. |
| 11,099,376 B1 | 8/2021 | Steier et al. |
| 11,103,320 B2 | 8/2021 | Leboeuf et al. |
| D930,162 S | 9/2021 | Cremer et al. |
| 11,109,762 B1 | 9/2021 | Steier et al. |
| 11,112,611 B1 | 9/2021 | Kessler et al. |
| 11,122,164 B2 | 9/2021 | Gigante |
| 11,123,604 B2 | 9/2021 | Fung |
| 11,129,562 B2 | 9/2021 | Roberts et al. |
| 11,132,055 B2 | 9/2021 | Jones et al. |
| 11,135,015 B2 | 10/2021 | Crawford et al. |
| 11,135,016 B2 | 10/2021 | Frielinghaus et al. |
| 11,137,610 B1 | 10/2021 | Kessler et al. |
| 11,141,221 B2 | 10/2021 | Hobeika et al. |
| 11,153,549 B2 | 10/2021 | Casas |
| 11,153,555 B1 | 10/2021 | Healy et al. |
| 11,163,176 B2 | 11/2021 | Karafin et al. |
| 11,164,324 B2 | 11/2021 | Liu et al. |
| 11,166,006 B2 | 11/2021 | Hegyi |
| 11,172,990 B2 | 11/2021 | Lang |
| 11,179,136 B2 | 11/2021 | Kohli et al. |
| 11,180,557 B2 | 11/2021 | Noelle |
| 11,181,747 B1 | 11/2021 | Kessler et al. |
| 11,185,891 B2 | 11/2021 | Cousins et al. |
| 11,202,682 B2 | 12/2021 | Staunton et al. |
| 11,207,150 B2 | 12/2021 | Healy et al. |
| 11,217,028 B2 | 1/2022 | Jones et al. |
| 11,224,763 B2 | 1/2022 | Takahashi et al. |
| 11,227,417 B2 | 1/2022 | Berlinger et al. |
| 11,244,508 B2 | 2/2022 | Kazanzides et al. |
| 11,253,216 B2 | 2/2022 | Crawford et al. |
| 11,253,323 B2 | 2/2022 | Hughes et al. |
| 11,257,190 B2 | 2/2022 | Mao et al. |
| 11,263,772 B2 | 3/2022 | Siemionow et al. |
| 11,269,401 B2 | 3/2022 | West et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt et al. |
| 11,284,846 B2 | 3/2022 | Graumann et al. |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,300,790 B2 | 4/2022 | Cheng et al. |
| 11,304,759 B2 | 4/2022 | Kovtun et al. |
| 11,307,402 B2 | 4/2022 | Steier et al. |
| 11,311,341 B2 | 4/2022 | Lang |
| 11,317,973 B2 | 5/2022 | Calloway et al. |
| 11,337,763 B2 | 5/2022 | Choi |
| 11,348,257 B2 | 5/2022 | Lang |
| 11,350,072 B1 | 5/2022 | Quiles Casas |
| 11,350,965 B2 | 6/2022 | Yilmaz et al. |
| 11,351,006 B2 | 6/2022 | Aferzon et al. |
| 11,360,315 B2 | 6/2022 | Tu et al. |
| 11,382,699 B2 | 7/2022 | Wassall et al. |
| 11,382,700 B2 | 7/2022 | Calloway et al. |
| 11,382,712 B2 | 7/2022 | Elimelech et al. |
| 11,382,713 B2 | 7/2022 | Healy et al. |
| 11,389,252 B2 | 7/2022 | Gera et al. |
| 11,432,828 B1 | 9/2022 | Lang |
| 11,432,931 B2 | 9/2022 | Lang |
| 11,452,568 B2 | 9/2022 | Lang |
| 11,460,915 B2 | 10/2022 | Frielinghaus et al. |
| 11,461,983 B2 | 10/2022 | Jones et al. |
| 11,464,581 B2 | 10/2022 | Calloway |
| 11,483,532 B2 | 10/2022 | Quiles Casas |
| 11,490,986 B2 | 11/2022 | Ben-Yishai |
| 11,648,016 B2 * | 5/2023 | Hathaway .......... A61B 17/1659 606/80 |
| 11,750,794 B2 | 9/2023 | Benishti et al. |
| 11,766,296 B2 | 9/2023 | Wolf et al. |
| 2002/0082498 A1 | 6/2002 | Wendt et al. |
| 2003/0059097 A1 | 3/2003 | Abovitz et al. |
| 2003/0117393 A1 | 6/2003 | Sauer et al. |
| 2003/0130576 A1 | 7/2003 | Seeley et al. |
| 2003/0210812 A1 | 11/2003 | Khamene et al. |
| 2003/0225329 A1 | 12/2003 | Rossner et al. |
| 2004/0019263 A1 | 1/2004 | Jutras et al. |
| 2004/0030237 A1 | 2/2004 | Lee et al. |
| 2004/0138556 A1 | 7/2004 | Cosman |
| 2004/0238732 A1 | 12/2004 | State et al. |
| 2005/0017972 A1 | 1/2005 | Poole et al. |
| 2005/0119639 A1 | 6/2005 | Mccombs et al. |
| 2005/0203380 A1 | 9/2005 | Sauer et al. |
| 2005/0215879 A1 | 9/2005 | Chuanggui |
| 2006/0134198 A1 | 6/2006 | Tawa et al. |
| 2007/0018975 A1 | 1/2007 | Chuanggui et al. |
| 2007/0058261 A1 | 3/2007 | Sugihara et al. |
| 2007/0183041 A1 | 8/2007 | Mccloy et al. |
| 2007/0233371 A1 | 10/2007 | Stoschek et al. |
| 2007/0273610 A1 | 11/2007 | Baillot |
| 2008/0002809 A1 | 1/2008 | Bodduluri |
| 2008/0007645 A1 | 1/2008 | McCutchen |
| 2008/0035266 A1 | 2/2008 | Danziger |
| 2008/0085033 A1 | 4/2008 | Haven et al. |
| 2008/0159612 A1 | 7/2008 | Fu et al. |
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2009/0018437 A1 | 1/2009 | Cooke |
| 2009/0036902 A1 | 2/2009 | Dimaio et al. |
| 2009/0062869 A1 | 3/2009 | Claverie et al. |
| 2009/0099445 A1 | 4/2009 | Burger |
| 2009/0123452 A1 | 5/2009 | Madison |
| 2009/0227847 A1 | 9/2009 | Tepper et al. |
| 2009/0300540 A1 | 12/2009 | Russell |
| 2010/0076305 A1 | 3/2010 | Maier-Hein et al. |
| 2010/0094308 A1 | 4/2010 | Tatsumi et al. |
| 2010/0106010 A1 | 4/2010 | Rubner et al. |
| 2010/0114110 A1 | 5/2010 | Taft et al. |
| 2010/0138939 A1 | 6/2010 | Bentzon et al. |
| 2010/0149073 A1 | 6/2010 | Chaum et al. |
| 2010/0274124 A1 | 10/2010 | Jascob et al. |
| 2011/0004259 A1 | 1/2011 | Stallings et al. |
| 2011/0098553 A1 | 4/2011 | Robbins et al. |
| 2011/0216060 A1 | 9/2011 | Weising et al. |
| 2011/0245625 A1 | 10/2011 | Trovato et al. |
| 2011/0254922 A1 | 10/2011 | Schaerer et al. |
| 2011/0306873 A1 | 12/2011 | Shenai et al. |
| 2012/0014608 A1 | 1/2012 | Watanabe |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0182605 A1 | 7/2012 | Hall et al. |
| 2012/0201421 A1 | 8/2012 | Hartmann et al. |
| 2012/0216411 A1 | 8/2012 | Wevers et al. |
| 2012/0238609 A1 | 9/2012 | Srivastava et al. |
| 2012/0289777 A1 | 11/2012 | Chopra et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0050258 A1 | 2/2013 | Liu et al. |
| 2013/0106833 A1 | 5/2013 | Fun |
| 2013/0135734 A1 | 5/2013 | Shafer et al. |
| 2013/0135738 A1 | 5/2013 | Shafer et al. |
| 2013/0190602 A1 | 7/2013 | Liao et al. |

(56) References Cited

U.S. PATENT DOCUMENTS

| | | |
|---|---|---|
| 2013/0209953 A1 | 8/2013 | Arlinsky et al. |
| 2013/0234914 A1 | 9/2013 | Fujimaki |
| 2013/0234935 A1 | 9/2013 | Griffith |
| 2013/0245461 A1 | 9/2013 | Maier-Hein et al. |
| 2013/0249787 A1 | 9/2013 | Morimoto |
| 2013/0249945 A1 | 9/2013 | Kobayashi |
| 2013/0265623 A1 | 10/2013 | Sugiyama et al. |
| 2013/0300637 A1 | 11/2013 | Smits et al. |
| 2013/0300760 A1 | 11/2013 | Sugano et al. |
| 2013/0342571 A1 | 12/2013 | Kinnebrew et al. |
| 2014/0031668 A1 | 1/2014 | Mobasser et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0105912 A1 | 4/2014 | Noelle |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | Mccarthy |
| 2014/0285404 A1 | 9/2014 | Takano et al. |
| 2014/0285429 A1 | 9/2014 | Simmons |
| 2014/0300632 A1 | 10/2014 | Laor |
| 2014/0300967 A1 | 10/2014 | Tilleman et al. |
| 2014/0301624 A1 | 10/2014 | Barckow et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter et al. |
| 2014/0340286 A1 | 11/2014 | Machida et al. |
| 2015/0018672 A1 | 1/2015 | Blumhofer et al. |
| 2015/0084990 A1 | 3/2015 | Laor |
| 2015/0150641 A1 | 6/2015 | Daon et al. |
| 2015/0182293 A1 | 7/2015 | Yang et al. |
| 2015/0192776 A1 | 7/2015 | Lee et al. |
| 2015/0209119 A1 | 7/2015 | Theodore et al. |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit et al. |
| 2015/0287236 A1 | 10/2015 | Winne et al. |
| 2015/0297314 A1 | 10/2015 | Fowler et al. |
| 2015/0310668 A1 | 10/2015 | Ellerbrock |
| 2015/0350517 A1 | 12/2015 | Duret et al. |
| 2015/0351863 A1 | 12/2015 | Plassky et al. |
| 2015/0363978 A1 | 12/2015 | Maimone et al. |
| 2015/0366620 A1 | 12/2015 | Cameron et al. |
| 2016/0022287 A1 | 1/2016 | Nehls |
| 2016/0030131 A1 | 2/2016 | Yang et al. |
| 2016/0086380 A1 | 3/2016 | Vayser et al. |
| 2016/0133051 A1 | 5/2016 | Aonuma et al. |
| 2016/0153004 A1 | 6/2016 | Zhang et al. |
| 2016/0175064 A1 | 6/2016 | Steinle et al. |
| 2016/0191887 A1 | 6/2016 | Casas |
| 2016/0228033 A1 | 8/2016 | Rossner |
| 2016/0249989 A1 | 9/2016 | Devam et al. |
| 2016/0256223 A1 | 9/2016 | Haimerl et al. |
| 2016/0302870 A1 | 10/2016 | Wilkinson et al. |
| 2016/0324580 A1 | 11/2016 | Esterberg |
| 2016/0324583 A1 | 11/2016 | Kheradpir et al. |
| 2016/0339337 A1 | 11/2016 | Ellsworth et al. |
| 2017/0014119 A1 | 1/2017 | Capote et al. |
| 2017/0027650 A1 | 2/2017 | Merck et al. |
| 2017/0031163 A1 | 2/2017 | Gao et al. |
| 2017/0068119 A1 | 3/2017 | Antaki et al. |
| 2017/0086941 A1 | 3/2017 | Marti et al. |
| 2017/0164919 A1 | 6/2017 | Lavallee et al. |
| 2017/0164920 A1 | 6/2017 | Lavallee et al. |
| 2017/0178375 A1 | 6/2017 | Benishti et al. |
| 2017/0220224 A1 | 8/2017 | Kodali et al. |
| 2017/0239015 A1 | 8/2017 | Sela et al. |
| 2017/0245944 A1 | 8/2017 | Crawford et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0348055 A1 | 12/2017 | Salcedo et al. |
| 2017/0348061 A1 | 12/2017 | Joshi et al. |
| 2017/0366773 A1 | 12/2017 | Kiraly et al. |
| 2017/0367766 A1 | 12/2017 | Mahfouz |
| 2017/0367771 A1 | 12/2017 | Tako et al. |
| 2017/0372477 A1 | 12/2017 | Penney et al. |
| 2018/0028266 A1 | 2/2018 | Barnes et al. |
| 2018/0049622 A1 | 2/2018 | Ryan et al. |
| 2018/0078316 A1 | 3/2018 | Schaewe et al. |
| 2018/0082480 A1 | 3/2018 | White et al. |
| 2018/0092667 A1 | 4/2018 | Heigl et al. |
| 2018/0092698 A1 | 4/2018 | Chopra et al. |
| 2018/0116732 A1 | 5/2018 | Lin et al. |
| 2018/0117150 A1 | 5/2018 | O'Dwyer et al. |
| 2018/0133871 A1 | 5/2018 | Farmer |
| 2018/0153626 A1 | 6/2018 | Yang et al. |
| 2018/0182150 A1 | 6/2018 | Benishti et al. |
| 2018/0185113 A1 | 7/2018 | Gregerson et al. |
| 2018/0193097 A1 | 7/2018 | Mclachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0303558 A1 | 10/2018 | Thomas |
| 2018/0317803 A1 | 11/2018 | Ben-Yishai et al. |
| 2018/0318035 A1 | 11/2018 | Mclachlin et al. |
| 2018/0368898 A1 | 12/2018 | Divincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0038365 A1 | 2/2019 | Soper et al. |
| 2019/0043238 A1 | 2/2019 | Benishti et al. |
| 2019/0046272 A1 | 2/2019 | Zoabi et al. |
| 2019/0053851 A1 | 2/2019 | Siemionow et al. |
| 2019/0069971 A1 | 3/2019 | Tripathi et al. |
| 2019/0105116 A1 | 4/2019 | Johnson et al. |
| 2019/0130792 A1 | 5/2019 | Rios et al. |
| 2019/0142519 A1 | 5/2019 | Siemionow et al. |
| 2019/0144443 A1 | 5/2019 | Jackson et al. |
| 2019/0175228 A1 | 6/2019 | Elimelech et al. |
| 2019/0192230 A1 | 6/2019 | Siemionow et al. |
| 2019/0200894 A1 | 7/2019 | Jung et al. |
| 2019/0201106 A1 | 7/2019 | Siemionow et al. |
| 2019/0216537 A1 | 7/2019 | Eltorai et al. |
| 2019/0254753 A1 | 8/2019 | Johnson et al. |
| 2019/0273916 A1 | 9/2019 | Benishti et al. |
| 2019/0310481 A1 | 10/2019 | Blum et al. |
| 2019/0333480 A1 | 10/2019 | Lang |
| 2019/0369717 A1 | 12/2019 | Frielinghaus et al. |
| 2019/0387351 A1 | 12/2019 | Lyren et al. |
| 2020/0015895 A1 | 1/2020 | Frielinghaus et al. |
| 2020/0019364 A1 | 1/2020 | Pond |
| 2020/0020249 A1 | 1/2020 | Jarc et al. |
| 2020/0038112 A1 | 2/2020 | Amanatullah et al. |
| 2020/0043160 A1 | 2/2020 | Mizukura et al. |
| 2020/0078100 A1 | 3/2020 | Weinstein et al. |
| 2020/0088997 A1 | 3/2020 | Lee et al. |
| 2020/0117025 A1 | 4/2020 | Sauer |
| 2020/0129058 A1 | 4/2020 | Li et al. |
| 2020/0129136 A1 | 4/2020 | Harding et al. |
| 2020/0129262 A1 | 4/2020 | Verard et al. |
| 2020/0129264 A1 | 4/2020 | Oativia et al. |
| 2020/0133029 A1 | 4/2020 | Yonezawa |
| 2020/0138618 A1 | 5/2020 | Roszkowiak et al. |
| 2020/0143594 A1 | 5/2020 | Lal et al. |
| 2020/0146546 A1 | 5/2020 | Chene et al. |
| 2020/0151507 A1 | 5/2020 | Siemionow et al. |
| 2020/0156259 A1 | 5/2020 | Ruiz et al. |
| 2020/0159313 A1 | 5/2020 | Gibby et al. |
| 2020/0163723 A1 | 5/2020 | Wolf et al. |
| 2020/0163739 A1 | 5/2020 | Messinger et al. |
| 2020/0178916 A1 | 6/2020 | Lalys et al. |

(56) References Cited

U.S. PATENT DOCUMENTS

| | | |
|---|---|---|
| 2020/0184638 A1 | 6/2020 | Meglan et al. |
| 2020/0186786 A1 | 6/2020 | Gibby et al. |
| 2020/0188028 A1 | 6/2020 | Feiner et al. |
| 2020/0188034 A1 | 6/2020 | Lequette et al. |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent et al. |
| 2020/0242280 A1 | 7/2020 | Pavloff et al. |
| 2020/0246074 A1 | 8/2020 | Lang |
| 2020/0246081 A1 | 8/2020 | Johnson et al. |
| 2020/0264451 A1 | 8/2020 | Blum et al. |
| 2020/0265273 A1 | 8/2020 | Wei et al. |
| 2020/0275988 A1 | 9/2020 | Johnson et al. |
| 2020/0286222 A1 | 9/2020 | Essenreiter et al. |
| 2020/0288075 A1 | 9/2020 | Bonin et al. |
| 2020/0305980 A1 | 10/2020 | Lang |
| 2020/0315734 A1 | 10/2020 | El Amm |
| 2020/0323460 A1 | 10/2020 | Busza et al. |
| 2020/0327721 A1 | 10/2020 | Siemionow et al. |
| 2020/0330179 A1 | 10/2020 | Ton |
| 2020/0341283 A1 | 10/2020 | Mccracken et al. |
| 2020/0355927 A1 | 11/2020 | Marcellin-Dibon et al. |
| 2020/0360091 A1 | 11/2020 | Murray et al. |
| 2020/0375666 A1 | 12/2020 | Murphy |
| 2020/0377493 A1 | 12/2020 | Heiser et al. |
| 2020/0377956 A1 | 12/2020 | Vogelstein et al. |
| 2020/0389425 A1 | 12/2020 | Bhatia et al. |
| 2020/0390502 A1 | 12/2020 | Holthuizen et al. |
| 2020/0390503 A1 | 12/2020 | Casas et al. |
| 2020/0402647 A1 | 12/2020 | Domracheva et al. |
| 2020/0409306 A1 | 12/2020 | Gelman et al. |
| 2020/0410687 A1 | 12/2020 | Siemionow et al. |
| 2020/0413031 A1 | 12/2020 | Khani et al. |
| 2021/0004956 A1 | 1/2021 | Book et al. |
| 2021/0009339 A1 | 1/2021 | Morrison et al. |
| 2021/0015560 A1 | 1/2021 | Boddington et al. |
| 2021/0015583 A1 | 1/2021 | Avisar et al. |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi et al. |
| 2021/0030511 A1 | 2/2021 | Wolf et al. |
| 2021/0038339 A1 | 2/2021 | Yu et al. |
| 2021/0049825 A1 | 2/2021 | Wheelwright et al. |
| 2021/0052348 A1 | 2/2021 | Stifter et al. |
| 2021/0065911 A1 | 3/2021 | Goel et al. |
| 2021/0077195 A1 | 3/2021 | Saeidi et al. |
| 2021/0077210 A1 | 3/2021 | Itkowitz et al. |
| 2021/0080751 A1 | 3/2021 | Lindsey et al. |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quaid et al. |
| 2021/0093417 A1 | 4/2021 | Liu |
| 2021/0104055 A1 | 4/2021 | Ni et al. |
| 2021/0107923 A1 | 4/2021 | Jackson et al. |
| 2021/0109349 A1 | 4/2021 | Schneider et al. |
| 2021/0109373 A1 | 4/2021 | Loo et al. |
| 2021/0110517 A1 | 4/2021 | Flohr et al. |
| 2021/0113269 A1 | 4/2021 | Vilsmeier et al. |
| 2021/0113293 A9 | 4/2021 | Silva et al. |
| 2021/0121238 A1 | 4/2021 | Palushi et al. |
| 2021/0137634 A1 | 5/2021 | Lang |
| 2021/0141887 A1 | 5/2021 | Kim et al. |
| 2021/0150702 A1 | 5/2021 | Claessen et al. |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing et al. |
| 2021/0165207 A1 | 6/2021 | Peyman |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0186647 A1 | 6/2021 | Elimelech et al. |
| 2021/0196404 A1 | 7/2021 | Wang |
| 2021/0223577 A1 | 7/2021 | Zhang et al. |
| 2021/0227791 A1 | 7/2021 | De et al. |
| 2021/0235061 A1 | 7/2021 | Hegyi |
| 2021/0248822 A1 | 8/2021 | Choi et al. |
| 2021/0274281 A1 | 9/2021 | Zhang et al. |
| 2021/0282887 A1 | 9/2021 | Wiggermann |
| 2021/0290046 A1 | 9/2021 | Nazareth et al. |
| 2021/0290336 A1 | 9/2021 | Wang |
| 2021/0290394 A1 | 9/2021 | Mahfouz |
| 2021/0295512 A1 | 9/2021 | Knoplioch et al. |
| 2021/0306599 A1 | 9/2021 | Pierce |
| 2021/0311322 A1 | 10/2021 | Belanger et al. |
| 2021/0314502 A1 | 10/2021 | Liu |
| 2021/0315636 A1 | 10/2021 | Akbarian et al. |
| 2021/0315662 A1 | 10/2021 | Freeman et al. |
| 2021/0325684 A1 | 10/2021 | Ninan et al. |
| 2021/0332447 A1 | 10/2021 | Lubelski et al. |
| 2021/0333561 A1 | 10/2021 | Oh et al. |
| 2021/0346115 A1 | 11/2021 | Dulin et al. |
| 2021/0349677 A1 | 11/2021 | Baldev et al. |
| 2021/0369226 A1 | 12/2021 | Siemionow et al. |
| 2021/0371413 A1 | 12/2021 | Thurston et al. |
| 2021/0373333 A1 | 12/2021 | Moon |
| 2021/0373344 A1 | 12/2021 | Loyola et al. |
| 2021/0378757 A1 | 12/2021 | Bay et al. |
| 2021/0386482 A1 | 12/2021 | Gera et al. |
| 2021/0389590 A1 | 12/2021 | Freeman et al. |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0071712 A1 | 3/2022 | Wolf et al. |
| 2022/0079675 A1 | 3/2022 | Lang |
| 2022/0121041 A1 | 4/2022 | Hakim |
| 2022/0133484 A1 | 5/2022 | Lang |
| 2022/0142730 A1 | 5/2022 | Wolf et al. |
| 2022/0155861 A1 | 5/2022 | Myung et al. |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0201274 A1 | 6/2022 | Achilefu et al. |
| 2022/0245400 A1 | 8/2022 | Siemionow et al. |
| 2022/0245821 A1 | 8/2022 | Ouzounis |
| 2022/0287676 A1 | 9/2022 | Steines et al. |
| 2022/0292786 A1 | 9/2022 | Pelzl et al. |
| 2022/0295033 A1 | 9/2022 | Quiles Casas |
| 2022/0304768 A1 | 9/2022 | Elimelech et al. |
| 2022/0358759 A1 | 11/2022 | Cork et al. |
| 2022/0405935 A1 | 12/2022 | Flossmann et al. |
| 2023/0027801 A1 | 1/2023 | Qian et al. |
| 2023/0034189 A1 | 2/2023 | Gera et al. |
| 2023/0290037 A1 | 9/2023 | Tasse et al. |
| 2023/0295302 A1 | 9/2023 | Bhagavatheeswaran et al. |
| 2023/0329799 A1 | 10/2023 | Gera et al. |
| 2023/0329801 A1 | 10/2023 | Elimelech et al. |

FOREIGN PATENT DOCUMENTS

| | | |
|---|---|---|
| CN | 103106348 A | 5/2013 |
| CN | 111915696 A | 11/2020 |
| CN | 112489047 A | 3/2021 |
| DE | 202004011567 U1 | 11/2004 |
| DE | 102004011567 A1 | 9/2005 |
| DE | 102014008153 A1 | 10/2014 |
| EP | 0933096 A2 | 8/1999 |
| EP | 1640750 A1 | 3/2006 |
| EP | 1757974 A1 | 2/2007 |
| EP | 2134847 A2 | 12/2009 |
| EP | 2891966 A1 | 7/2015 |

(56) References Cited

FOREIGN PATENT DOCUMENTS

| | | |
|---|---|---|
| EP | 3034607 A1 | 6/2016 |
| EP | 3076660 A1 | 10/2016 |
| EP | 2654749 B1 | 5/2017 |
| EP | 3216416 A1 | 9/2017 |
| EP | 2032039 B1 | 10/2017 |
| EP | 3224376 A1 | 10/2017 |
| EP | 3247297 A1 | 11/2017 |
| EP | 3123970 B1 | 4/2018 |
| EP | 2030193 B1 | 7/2018 |
| EP | 2892558 B1 | 4/2019 |
| EP | 2635299 B1 | 7/2019 |
| EP | 3505050 A1 | 7/2019 |
| EP | 2875149 B1 | 12/2019 |
| EP | 3593227 A1 | 1/2020 |
| EP | 3634294 A1 | 4/2020 |
| EP | 3206583 B1 | 9/2020 |
| EP | 2625845 B1 | 3/2021 |
| EP | 3789965 A1 | 3/2021 |
| EP | 3858280 A1 | 8/2021 |
| EP | 3952331 A1 | 2/2022 |
| GB | 2507314 A | 4/2014 |
| IN | 101379412 A | 3/2009 |
| KR | 10-2014-0120155 A | 10/2014 |
| WO | 03/34705 A2 | 4/2003 |
| WO | 2006/002559 A1 | 1/2006 |
| WO | 2007/051304 A1 | 5/2007 |
| WO | 2007/115826 A2 | 10/2007 |
| WO | 2008/103383 A1 | 8/2008 |
| WO | 2010/067267 A1 | 6/2010 |
| WO | 2010/074747 A1 | 7/2010 |
| WO | 2012/061537 A2 | 5/2012 |
| WO | 2012/101286 A1 | 8/2012 |
| WO | 2013/112554 A1 | 8/2013 |
| WO | 2014/014498 A1 | 1/2014 |
| WO | 2014/024188 A1 | 2/2014 |
| WO | 2014/037953 A2 | 3/2014 |
| WO | 2014/113455 A1 | 7/2014 |
| WO | 2014/125789 A1 | 8/2014 |
| WO | 2014/167563 A1 | 10/2014 |
| WO | 2014/174067 A1 | 10/2014 |
| WO | 2015/058816 A1 | 4/2015 |
| WO | 2015/061752 A1 | 4/2015 |
| WO | 2015/109145 A1 | 7/2015 |
| WO | 2016/151506 A1 | 9/2016 |
| WO | 2018/052966 A1 | 3/2018 |
| WO | 2018/073452 A1 | 4/2018 |
| WO | 2018/200767 A1 | 11/2018 |
| WO | 2018/206086 A1 | 11/2018 |
| WO | 2019083431 A1 | 5/2019 |
| WO | 2019/161477 A1 | 8/2019 |
| WO | 2019/195926 A1 | 10/2019 |
| WO | 2019/210353 A1 | 11/2019 |
| WO | 2019/211741 A1 | 11/2019 |
| WO | 2020/109903 A1 | 6/2020 |
| WO | 2020/109904 A1 | 6/2020 |
| WO | 2021/017019 A1 | 2/2021 |
| WO | 2021/019369 A1 | 2/2021 |
| WO | 2021/021979 A2 | 2/2021 |
| WO | 2021/023574 A1 | 2/2021 |
| WO | 2021/046455 A1 | 3/2021 |
| WO | 2021/048158 A1 | 3/2021 |
| WO | 2021/061459 A1 | 4/2021 |
| WO | 2021/062375 A1 | 4/2021 |
| WO | 2021/073743 A1 | 4/2021 |
| WO | 2021/087439 A1 | 5/2021 |
| WO | 2021/091980 A1 | 5/2021 |
| WO | 2021/112918 A1 | 6/2021 |
| WO | 2021/130564 A1 | 7/2021 |
| WO | 2021/137752 A1 | 7/2021 |
| WO | 2021/141887 A1 | 7/2021 |
| WO | 2021/145584 A1 | 7/2021 |
| WO | 2021/154076 A1 | 8/2021 |
| WO | 2021/183318 A2 | 9/2021 |
| WO | 2021/188757 A1 | 9/2021 |
| WO | 2021/255627 A1 | 12/2021 |
| WO | 2021/257897 A1 | 12/2021 |
| WO | 2021/258078 A1 | 12/2021 |
| WO | 2022/009233 A1 | 1/2022 |
| WO | 2022/053923 A1 | 3/2022 |
| WO | 2022/079565 A1 | 4/2022 |
| WO | 2023/281395 A1 | 1/2023 |
| WO | 2023/007418 A1 | 2/2023 |
| WO | 2023/021448 A1 | 2/2023 |
| WO | 2023/021450 A1 | 2/2023 |
| WO | 2023/021451 A1 | 2/2023 |
| WO | 2023/026229 A1 | 3/2023 |
| WO | 2023/047355 A1 | 3/2023 |

* cited by examiner

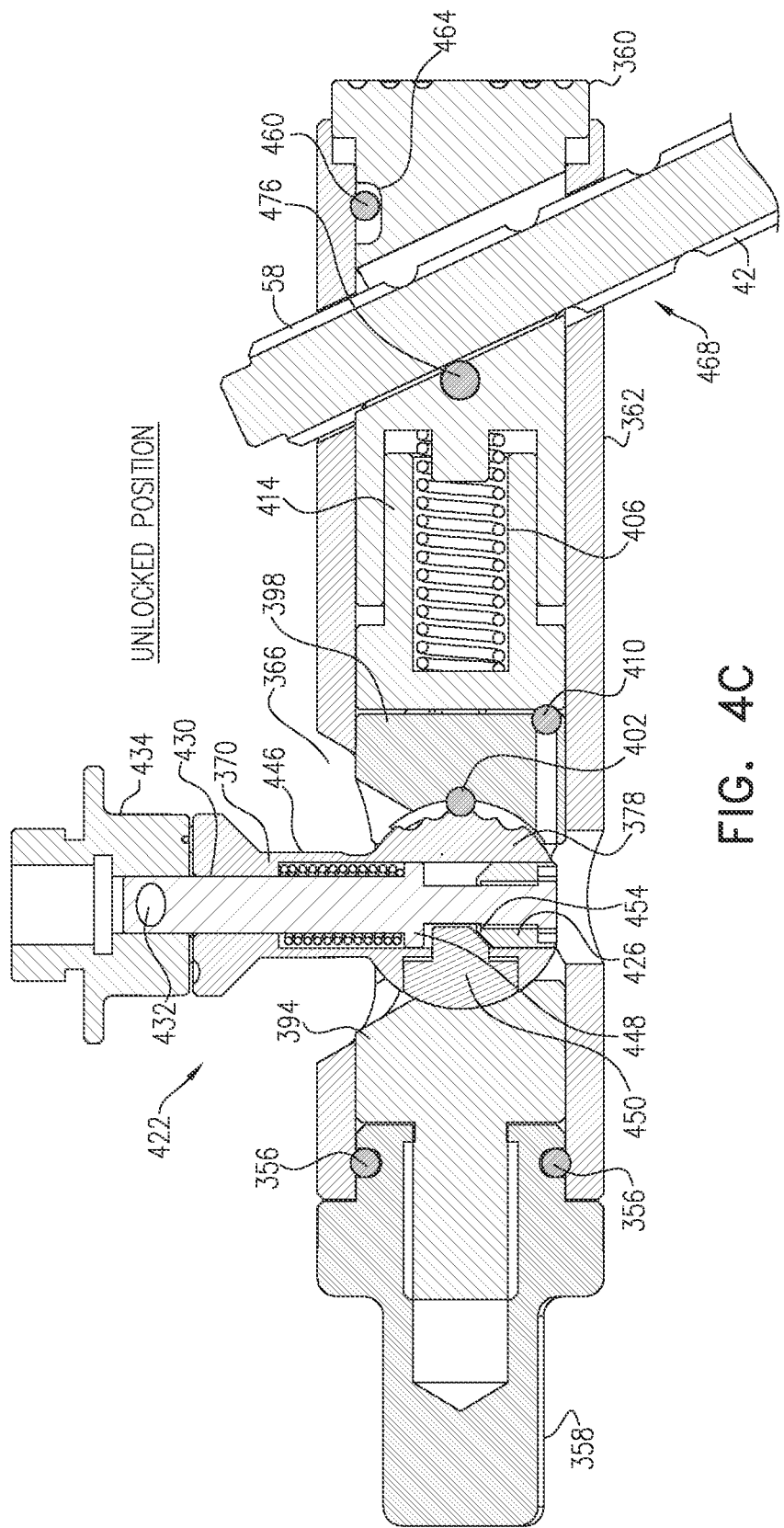

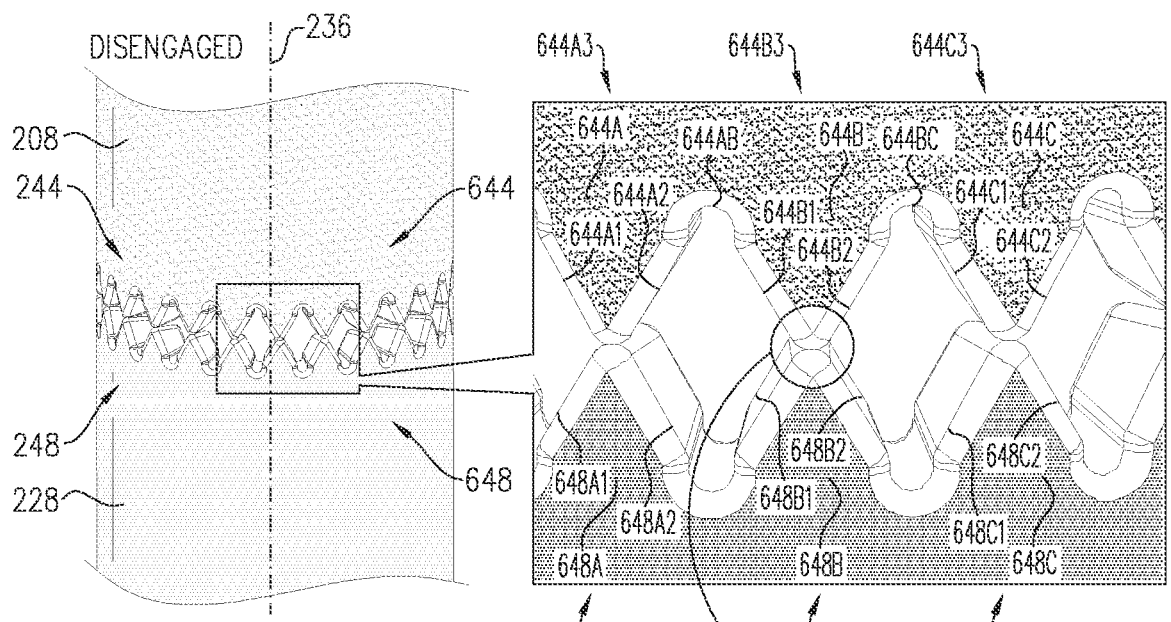
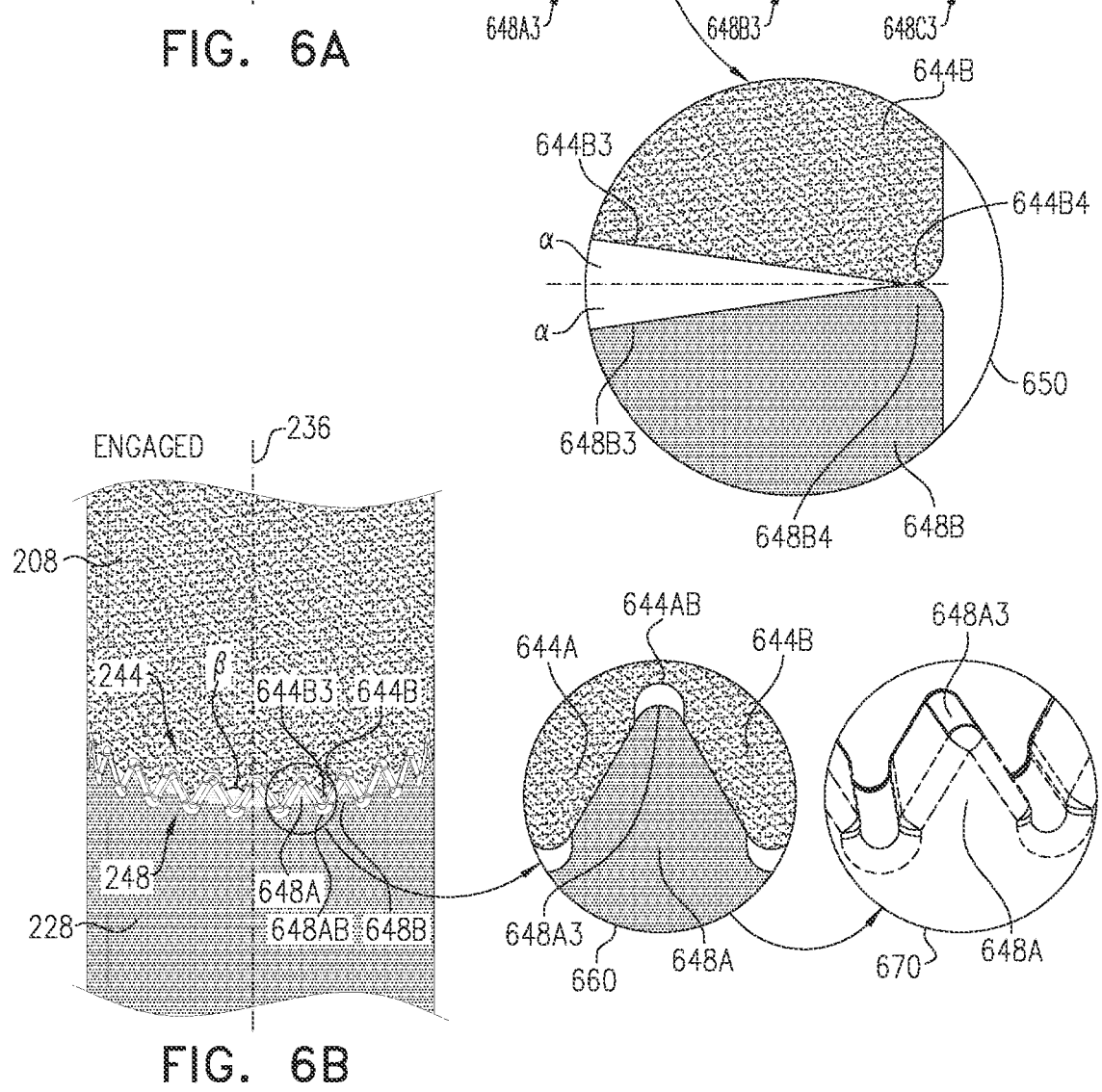
FIG. 6A
FIG. 6B

ILIAC PIN AND ADAPTER

FIELD OF THE INVENTION

The present invention relates generally to surgery, and specifically to surgery performed using augmented reality.

BACKGROUND OF THE INVENTION

In an augmented reality system used by a physician performing surgery, it is typically necessary to register a frame of reference of a patient with a frame of reference of the augmented reality system used by the physician. Methods for registration are known in the art.

U.S. Pat. Nos. 7,835,734 and 3,467,351 to Mire et al. describe a dynamic reference frame that can be used to maintain localization of a patient space with an image space. The dynamic reference frame can be fixedly interconnected with a bone portion of the anatomy of the patient.

U.S. Pat. No. 9,066,151 to Sasso describes mounting a surgical navigation reference frame to a patient. A bone anchor having a bone engaging portion is inserted through a cannula for anchoring to bone. The bone anchor cooperates with the cannula to form a mounting device that is adapted for coupling with the surgical navigation reference frame.

U.S. Pat. No. 9,339,448 to Reckling, et al. describes placement of an implant into bone, such across the sacroiliac joint. It is stated that placement can be facilitated using various CT imaging views that allow the implants to be placed in bone associated with articular cartilage.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus for mounting in a bone of a patient, including:
  a rigid elongated member having an axis of symmetry and a distal section, a proximal section, and an intermediate section connecting the distal and proximal sections; and
  n helical blades, formed in the distal section, distributed symmetrically about the axis, each of the blades having a helix angle greater than zero and less than 45°, and wherein a cross-section of the distal section, taken orthogonally to the axis of symmetry, has n mirror planes containing the axis of symmetry, wherein n is a whole number greater than one, wherein the blades are configured to penetrate into the bone and engage stably therein.

In a disclosed embodiment the n helical blades taper by respective tapering planes to a common point at a distal tip of the section, so that the distal tip acts as a dilator.

In a further disclosed embodiment the n helical blades are configured to connect with the intermediate section in curved surfaces, so that the curved surfaces act as a support shoulder section when the blades penetrate the bone.

In a yet further disclosed embodiment the n helical blades have n respective edges, and the n respective edges are in the form of n cylindrical helices.

In an alternative embodiment the n helical blades have n respective edges, and the n respective edges are in the form of n conical helices.

In a further alternative embodiment the apparatus includes a plurality of ribs, formed on an outer surface of the proximal section, each of the ribs being parallel to the axis of symmetry. The apparatus may include an adapter, having multiple independent modes of motion, that is configured to accept an alignment target for the patient, wherein the ribs are configured to removably engage the adapter.

In a yet further alternative embodiment the helix angle is configured so as to require a preselected force for extraction of the rigid member when the blades penetrate the bone, and the preselected force is a metric of a stability of the member.

There is further provided, according to an embodiment of the inventions, an adapter for coupling a pin to a marker, including:
  a cross-piece formed of a first cylindrical structure having a first axis of symmetry, intersecting a second cylindrical structure having a second axis of symmetry, the two axes of symmetry intersecting orthogonally;
  a wedge, disposed in the first cylindrical structure, comprising a wedge plane surface;
  a wedge receiver, disposed in the second cylindrical structure, consisting of a receiver plane surface parallel to and contacting the wedge plane surface, so that the wedge and the wedge receiver engage;
  a pin grip having a cylindrical grip axis of symmetry, connected to the wedge receiver so that the cylindrical grip axis of symmetry and the second axis of symmetry are congruent, the pin grip including a first aperture, having a third axis of symmetry orthogonal to the cylindrical grip axis of symmetry, configured to receive the pin;
  a receiving base holder including a second cylindrical section, having a receiver axis of symmetry, connected to the second cylindrical structure so that the receiver axis of symmetry and the second axis of symmetry are congruent, the receiving base holder including a second aperture configured to retain a receiving base able to receive the marker; and
  a lock, connected to the wedge, which in a lock position translates the wedge so that the wedge plane surface contacts the receiver plane surface in a first contact area, so as to lock the pin grip with respect to the first axis of symmetry, the pin with respect to the third axis of symmetry, and the receiving base holder with respect to the second axis of symmetry, and in an unlock position translates the wedge so that the wedge plane surface contacts the receiver plane surface in a second contact area less than the first contact area, so as to permit the pin grip to rotate about the first axis of symmetry, the pin to move with respect to the third axis of symmetry, and the receiving base holder to rotate about the second axis of symmetry.

Movement of the pin with respect to the third axis of symmetry may consist of translation of the pin along the third axis and/or rotation of the pin around the third axis.

The second aperture may define a fourth axis of symmetry, the adapter including:
  a further lock connected via a supporting rod, disposed in the second aperture along the fourth axis of symmetry, to the receiving base.

In an unlocked position of the further lock the receiving base may be free to rotate around the fourth axis of symmetry.

In a locked position of the further lock the receiving base may be unable to rotate around the fourth axis of symmetry.

The adapter may include a pin holder configured to retain the pin grip and having a first set of teeth, and the first cylindrical structure may have a second set of teeth congruent with and configured to mate with the first set of teeth.

There is further provided, according to an embodiment of the present invention, an adapter for coupling a pin to one of a registration marker and a patient marker, including:
- a cylindrical housing, including a first aperture and a second aperture therein, having a cylindrical housing axis of symmetry;
- a receiving base mount including a cylindrical section fixedly attached to a spherical ball disposed within the housing so that the cylindrical section penetrates the first aperture, the cylindrical section having a mount axis of symmetry;
- a receiving base support having a cylindrical receiving base support axis of symmetry, and having a first termination and a second termination including a conical section, the support being disposed within the receiving base mount so that the receiving base support axis of symmetry aligns with the mount axis of symmetry;
- a receiving base coupled rotatably to the first termination of the receiving base support;
- a wedge, comprising a plane face, disposed within the cylindrical housing so that the plane face contacts a conical face of the conical section;
- a pin retainer including a pin opening, coupled to the wedge, and disposed within the cylindrical housing so that the pin opening aligns with the second aperture of the housing; and
- a lock, attached to the cylindrical housing, which in a locked state translates the wedge along the cylindrical housing axis of symmetry so that the plane face thereof is a preselected distance from the receiving base support axis of symmetry, thereby preventing rotation of the receiving base, rotation of the receiving base mount, and motion of the pin when disposed in the pin opening, and which in an unlocked state translates the wedge along the cylindrical housing axis of symmetry so that the plane face thereof is at a greater distance than the preselected distance from the receiving base axis of symmetry, thereby permitting rotation of the receiving base, rotation of the receiving base mount, and motion of the pin when disposed in the pin opening.

In a disclosed embodiment the spherical ball includes a first plane surface, the adapter further including a mount holder, disposed within the cylindrical housing, having a second plane surface that mates with the first plane surface so as to constrain the rotation of the receiving base mount to be parallel to the plane surfaces. The spherical ball may include a plurality of valleys orthogonal to the first plane surface, and the mount holder may include a pin configured to mate with a selected one of the valleys.

Typically, the lock in the locked state prevents the rotation of the receiving base mount and locks the mount in a position according to the selected one of the valleys.

Typically, the lock in the unlocked state permits the rotation of the receiving base mount from a position determined by the selected one of the valleys.

In a further disclosed embodiment the mount holder includes a third plane surface orthogonal to the housing axis of symmetry, the third plane surface including a plurality of spheres distributed symmetrically around the housing axis of symmetry, the adapter including a mount holder retainer, disposed in the cylindrical housing, having a retainer surface parallel to the third plane surface and including a plurality of sets of indentations distributed symmetrically around the housing axis of symmetry, wherein the plurality of spheres are configured to mate with selected ones of the indentations.

Typically, the lock in the locked state prevents the rotation of the receiving base mount and locks the mount in a position according to the selected ones of the indentations.

Typically, the lock in the unlocked state permits the rotation of receiving base mount from a position determined by the selected ones of the indentations.

The present disclosure will be more fully understood from the following detailed description of the embodiments thereof, taken together with the drawings, in which:

BRIEF DESCRIPTION OF THE DRAWINGS

FIGS. 4A, 4B, 4C, and 4D are schematic diagrams of an adapter, according to an alternative embodiment of the present invention;

FIGS. 6A and 6B are schematic figures of mating teeth implemented in an adapter, according to an embodiment of the present invention.

DETAILED DESCRIPTION OF EMBODIMENTS

Overview

Figure 1:
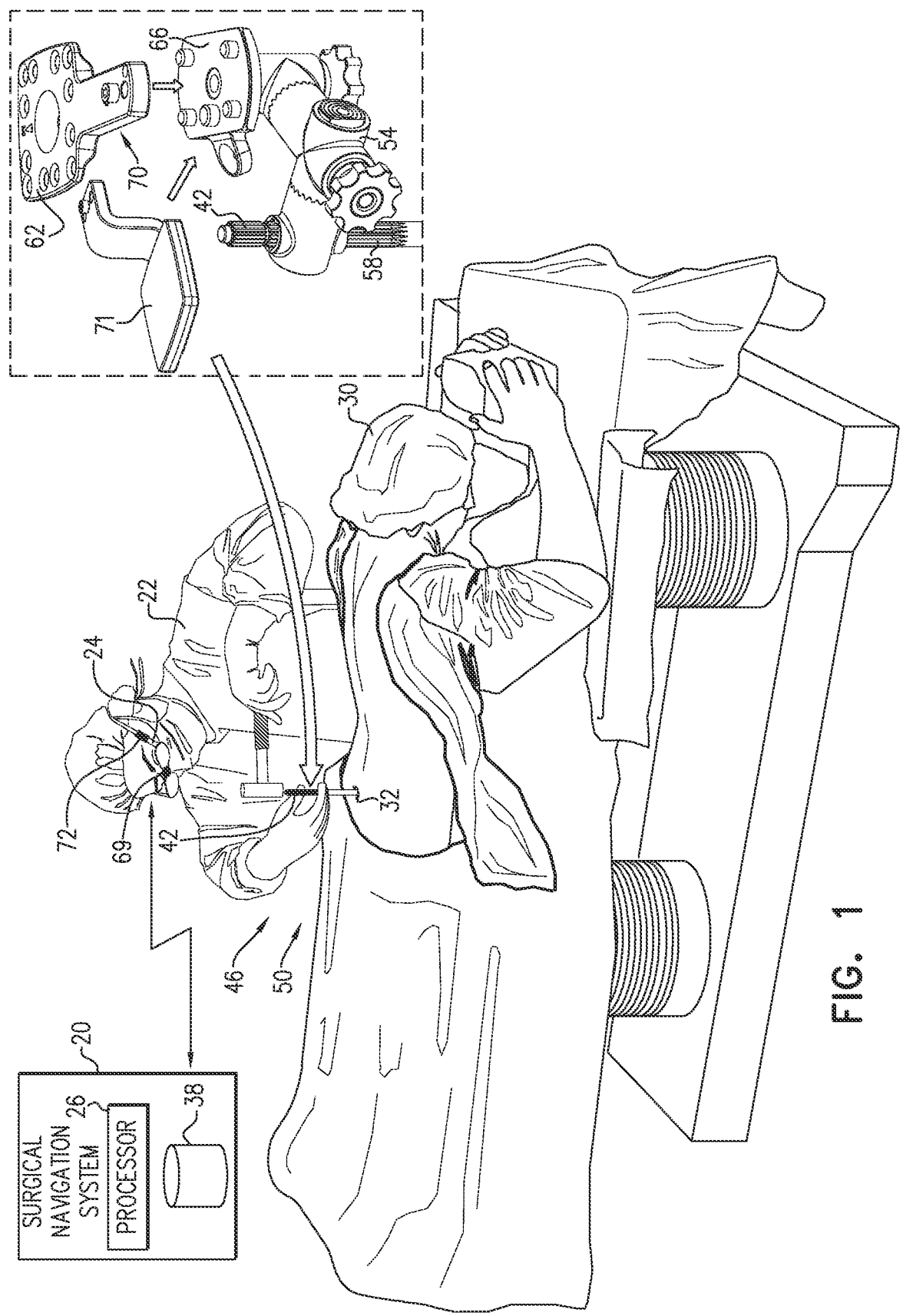
FIG. 1 is a schematic illustration of a medical procedure, according to an embodiment of the present invention.

In a medical procedure using augmented reality, it is typically necessary to initially register a position of a patient undergoing the procedure with an augmented reality assembly, optionally being worn by a professional performing the procedure (e.g., by using Head Mounted Display systems). During the procedure, the registration then enables images generated within the assembly to be aligned with the patient, as a location of the patient is determined and/or tracked.

The localization and/or tracking is typically performed by rigidly anchoring a marker, e.g., a patient marker to the patient, typically to a bone of the patient. Once the patient marker has been so anchored, the augmented reality assembly may acquire images of the marker, in real time, so as perform the required localization and/or tracking.

Embodiments of the present invention provide a pin which may be rigidly inserted into the bone of the patient such as the iliac bone or iliac crest and the posterior superior iliac spine, for performing spine related medical procedures, for example. Embodiments of the invention also provide an adjustable adapter which can couple to the pin, and to which can also be attached the patient marker. (The pin may also be used to receive a registration marker, for the earlier registration stage referred to above, or any other marker used, e.g., for localization, detection and/or tracking.) Typically, the professional may adjust the adapter so that the attached patient marker is in a location permitting images of the marker to be acquired by the assembly.

In embodiments of the present invention the pin comprises a plurality of helical blades, the blades being configured to penetrate a selected bone of the patient. Forming the blades to be helical enhances the stability of the pin, once the blades are within the bone, compared to prior art pins having straight blades. The enhancement in stability is because a non-zero helical angle of the blades requires an increase in the force required to extract the pin. The increase depends, in a monotonically increasing manner, on a value of the helical angle.

In embodiments of the present invention the adapter has five degrees of freedom, providing five independent modes of motion, the different modes of motion facilitating adjustment of the position of the attached patient marker as well as the registration marker. In a disclosed embodiment the adapter has two locks, a first lock locking four of the modes of motion simultaneously, a second lock locking the fifth mode motion. In an alternative disclosed embodiment the adapter has one lock which locks all five modes of motion simultaneously.

System Description

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Reference is now made to FIG. 1, which is a schematic illustration of a medical procedure, according to an embodiment of the present invention. During the procedure, performed by a professional 22, the professional uses a surgical navigation system 20, which assists the professional in performance of the procedure. Surgical navigation system 20 comprises a processor 26, which operates elements of the system, and which communicates with an augmented reality assembly 24, worn by professional 22, that is incorporated in the system. While assembly 24 may be incorporated for wearing into a number of different retaining structures on professional 22, in the present description the retaining structure is assumed to be similar to a pair of spectacles. Those having ordinary skill in the augmented reality art will be aware of other possible structures, such as incorporation of the augmented reality assembly into a head-up display that is integrated into a helmet worn by the user of system 20, and all such structures are assumed to be comprised within the scope of the present invention. One such head-up display is described below with reference to FIG. 7.

In one embodiment processor 26 is assumed to be incorporated within a stand-alone computer, and the processor typically communicates with other elements of the system, including assembly 24, wirelessly, as is illustrated in FIG. 1. Alternatively or additionally, processor 26 may use optical and/or conducting cables for the communication. In further alternative embodiments processor 26 is integrated within assembly 24, or in the mounting of the assembly. Processor 26 is typically able to access a database 38, wherein are stored images and other visual elements used by system 20. Software enabling processor 26 to operate system 20 may be downloaded to the processor in electronic form, over a network, for example. Alternatively or additionally, the software may be provided on non-transitory tangible media, such as optical, magnetic, or electronic storage media.

Assembly 24 comprises, inter alia, one or more image capturing devices 72, also termed herein a camera 72.

According to some aspects, image capturing device 72 is configured to capture images in the infra-red spectrum. Assembly 24 may then also comprise an infra-red projector 69. Assembly 24 and functions of system 20, processor 26, projector 69, and device 72 are described below. An assembly similar to augmented reality assembly 24, and its operation, are described in U.S. Pat. No. 9,928,629, to Benishti, et al., whose disclosure is incorporated herein by reference.

The medical procedure exemplified here is performed on a patient 30, and during an initial stage of the procedure professional 22 makes an incision 32 into the patient's back. The professional then inserts a pin 42 into the incision, with minimal damage, so that a distal tip 46 of the pin contacts a desired point on a surface of a bone of the patient. In some embodiments the pin is inserted to the bone surface via a cannula (not shown in the figure). In some embodiments the desired point is on an iliac crest of the patient's ilium, so that pin 42 is also referred to herein as iliac pin 42. The structure and operation of pin 42 is described in more detail below.

It will be understood that pin 42 may be inserted with or without a cannula. Even without a cannula, distal tip 46 facilitates the entry of the pin with minimal damage, and the tip acts as a dilator.

Once distal tip 46 contacts the bone surface desired point, professional 22 may hammer pin 42 into the contacted bone, as shown schematically in the figure. Pin 42 is hammered in until a distal section 50 of the pin enters the bone so that the pin stably engages with the bone. When the pin is stably engaged with the bone, professional 22 may insert an adapter 54 to mate with a proximal section 58 of pin 42. The structure and operation of adapter 54 is described in more detail below.

As is apparent from the construction of distal section 50, described below, as the distal section enters the bone, the pin rotates slightly. The rotation contributes to the stable engagement of the pin with the bone, by increasing the extraction force required for the pin, by virtue of its helical blades, compared to the force required for a pin with straight blades. The increase in stability is described below, with reference to FIG. 5, and contributes to a bidirectional bone anchoring mechanism, also described below.

The professional attaches an alignment target 62 to a receiving base 66 of the adapter, the target when attached to the base operating as a patient marker 70. Patient marker 70 thus comprises alignment target 62 coupled to base 66. As is described below, patient marker 70 is used by system 20 to determine the position and orientation of patient 30 during the medical procedure.

In some embodiments, prior to attaching patient marker 70 to receiving base 66, a registration marker 71 is attached to the receiving base, when the pin engages the patient bone. Registration marker 71 comprises elements which may be imaged fluoroscopically, and which are in a known pre-set dimensional relationship with each other. Imaging registration marker 71 and patient 30 fluoroscopically, typically by computerized tomography (CT), enables the marker to be registered with the patient. The registration is used in the tracking of patient 30 that is described below.

A marker similar to registration marker 71 is described in U.S. Patent Application 2021/0030511 which is incorporated herein by reference.

In system 20, marker 70 may be tracked using images acquired by device 72, the images being formed in response to infra-red radiation produced by projector 69.

FIGS. 2A, 2B, 2C, and 2D are schematic diagrams of iliac pin 42, according to an embodiment of the present invention. Pin 42 is a rigid elongated member, also herein termed a rod, having a central axis of symmetry 74, that is generally cylindrical. In one embodiment pin 42 is formed from titanium alloy, and in a disclosed embodiment the pin has an outside diameter of approximately 6 mm and a length of approximately 150 mm. However, it will be understood that other embodiments may have outside diameters and lengths that are greater or smaller than those of the disclosed embodiment.

Pin 42 is formed in three sections: distal section 50, which acts as a bone engaging section, and is also referred to herein as bone engaging section 50; a proximal section 58, which acts an adapter receiving section, and is also referred to herein as adapter receiving section 58; and a central section 56 which connects the distal and proximal sections.

Figure 2A:
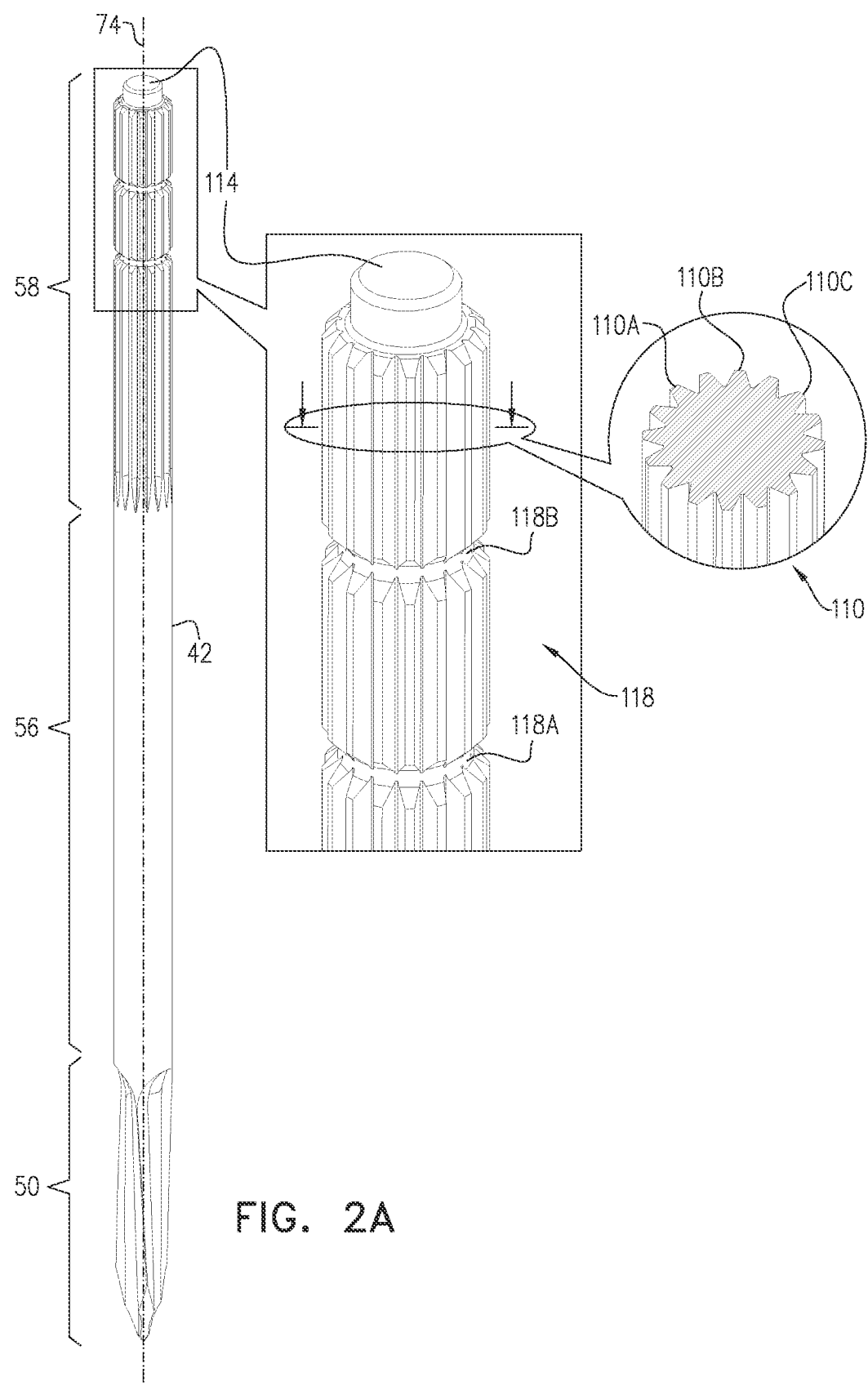
FIGS. 2A, 2B, 2C, and 2D are schematic diagrams of an iliac pin, according to an embodiment of the present invention.
Figure 2B:
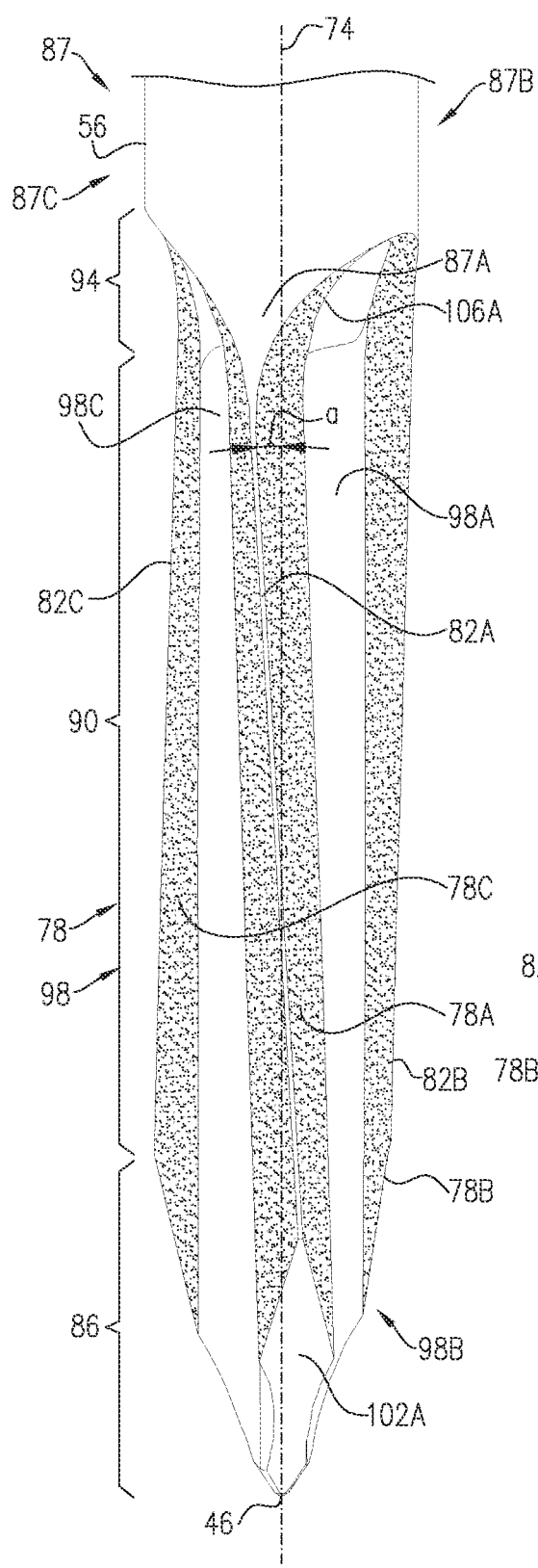

FIG. 2B illustrates distal section 50 of pin 42, the distal section being comprised of three regions: a distal region 86, a central region 90, and a proximal region 94. In one embodiment section 50 has a length of 32 mm, but other embodiments may have lengths of section 50 larger or smaller than 32 mm.

Central region 90 comprises a plurality of two or more substantially similar sharp helical blades 78A, 78B, 78C, . . . separated by the same number of helical undercuts 98A, 98B, 98C, . . . , also herein termed grooves 98A, 98B, 98C, . . . and the blades and grooves are distributed symmetrically around central axis 74. Blades 78A, 78B, 78C, . . . and grooves 98A, 98B, 98C, . . . are generically referred to herein as blades 78 and grooves 98. In the description herein pin 42 is assumed to comprise three blades 78 and grooves 98, and those with ordinary skill in the art will be able to adapt the description, mutatis mutandis, for numbers of helical blades and grooves other than three.

Figure 2C:
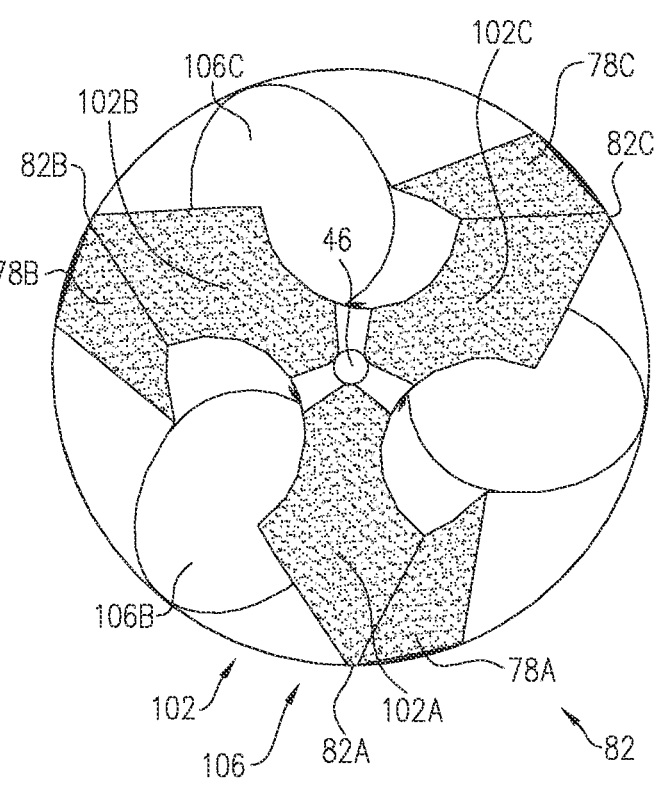
Figure 2D:
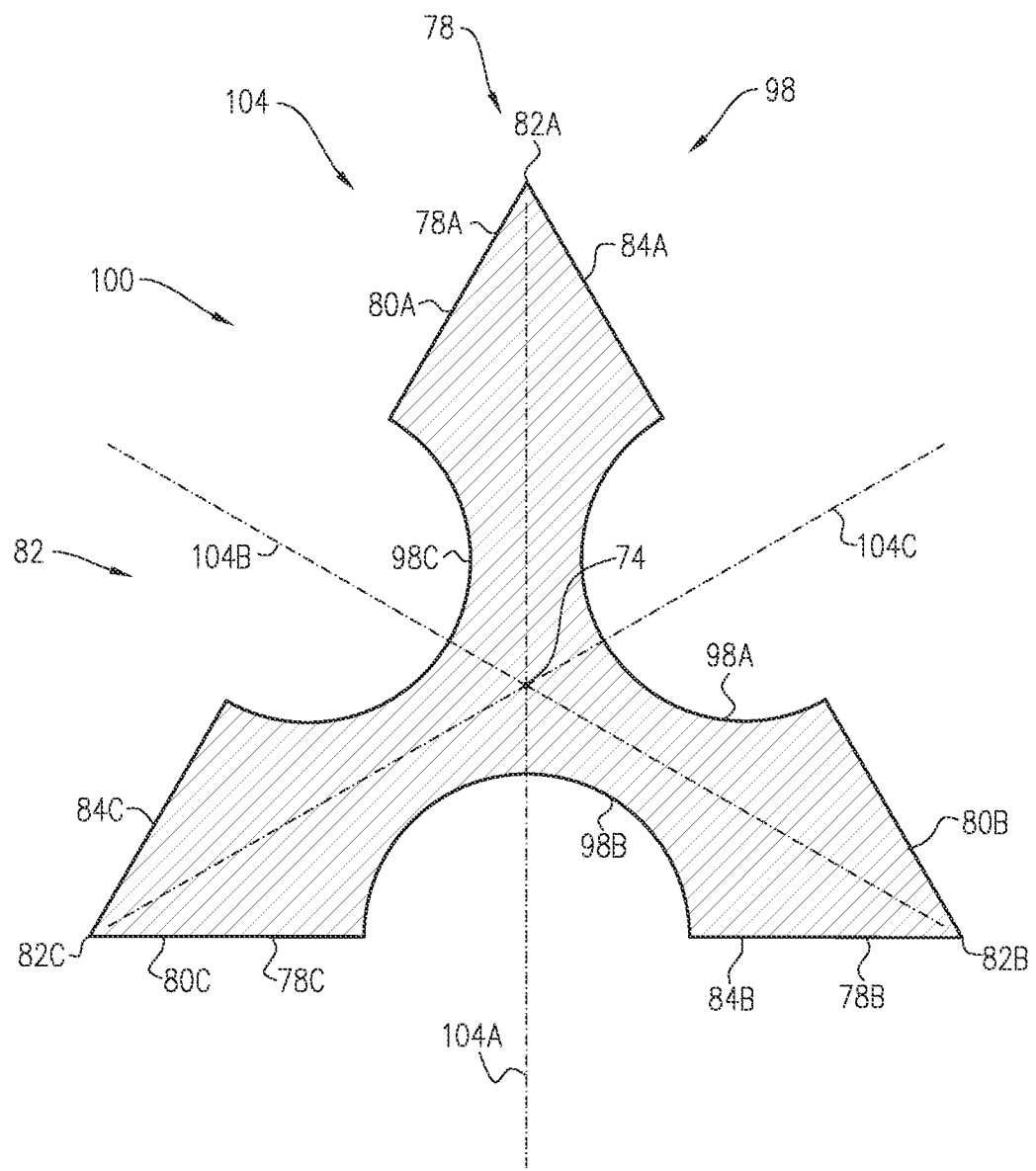

FIG. 2D illustrates a cross-section 100 of central region 90, taken orthogonally to axis 74 and the cross-section has rotational symmetry and also has mirror symmetry. For the three blades and grooves of the illustrated embodiment, there is three-fold rotational symmetry, and three mirror planes 104A, 104B, 104C. In general, embodiments with n blades, where n is a whole number equal to or greater than 2, have cross-sections for their central region with n-fold rotational symmetry and n mirror planes.

As is also illustrated in FIG. 2D, in central section 90 each helical blade 78A, 78B, 78C, . . . is respectively comprised of two planes 80A, 84A; 80B, 84B; 80C, 84C; . . . meeting at respective helical sharp edges 82A, 82B, 82C, . . . generically termed edges 82. In one embodiment a helix angle α of blades 78 (illustrated in FIG. 2B), and of their edges 82, is approximately 3° for a pin with approximate diameter 6 mm, and the edges meet at an approximate angle of 60°. In general, embodiments of the invention have a non-zero helix angle that is less than 45°. Helix angle α corresponds to the angle made by an orthogonal projection of edge 82 onto a plane comprising axis of symmetry 74. Typically, each edge 82 is a cylindrical helix, so that the distance from each point on a given edge to axis 74 is constant. In some embodiments each edge 82 is a conical helix, wherein the distance from a given point on the edge to axis 74 reduces monotonically as the given point moves distally, i.e., towards distal section 86.

As shown in FIG. 2C, which is a view of distal tip 46 along axis 74 from below the tip, in distal section 86 each blade 78A, 78B, 78C, . . . is respectively tapered by a tapering plane 102A, 102B, 102C, . . . , generically termed tapering planes 102. Tapering planes 102 meet at a common point, i.e., distal tip 46. In one embodiment each plane 102 makes an angle of approximately 20° with axis 74. By forming blades 78 to meet at a common point, section 86 may act as a trocar or a dilator, and is also referred to herein as dilator section 86.

In proximal section 94 planes 80A, 84A; 80B, 84B; 80C, 84C; . . . are curved so that grooves 98A, 98B, 98C, . . . meet with central section 56 in curved surfaces, typically respective partially spherical or non-spherical surfaces 106A, 106B, 106C, . . . , generically termed surfaces 106. In use of pin 42, once it engages with a bone, the curved portions of planes 80A, 84A; 80B, 84B; 80C, 84C; . . . , together with surfaces 106, act as a support shoulder for the pin, so that section 94 is also referred to herein as support shoulder section 94.

As stated above, in support shoulder section 94 planes 80A, 84A; 80B, 84B; 80C, 84C; . . . are curved, so that each pair of planes as they curve forms a respective wedge 87A; 87B; 87C; . . . (illustrated in FIG. 2B). Wedges 87A, 87B, 87C, . . . , generically termed wedges 87, act as terminations of sharp edges 82A, 82B, 82C, . . . . When pin 42 is inserted in a bone of patient 30, blades 78 are able to penetrate the bone until wedges 87 enter the bone. As they enter the bone the wedges force the bone to separate, so there is a countervailing force from surfaces 106 on the wedges that both prevents further penetration of pin 42 into the bone and that acts to stabilize and anchor the pin in position.

In addition, the helical configuration of blades 78 increases the resistance to extraction of pin 42 from the bone (compared to straight blades). Consequently, the combination of the helically configured blades and the wedge terminations of the edges of the blades operates to stably anchor the pin against penetration and extraction, i.e., as the bidirectional bone anchoring mechanism referred to above.

Adapter receiving section 58 comprises a plurality of substantially similar ribs 110A, 110B, 110C, . . . generically termed ribs 110, formed on the outer surface of pin 42. Ribs 110 are parallel to axis 74 and are distributed symmetrically about the axis. In one embodiment there are 16 ribs 110 having a height of approximately 670 μm formed on the outer surface of pin 42, but other embodiments may have different numbers of ribs, as well as different rib heights. Section 58 terminates proximally in a plane disclike region 114, and it is this region that professional 22 hammers on when inserting pin 42 into the bone of a patient, to prevent rib deformation.

Formed within ribs 110 are a plurality of circular grooves 118A, 118B, . . . , each groove being orthogonal to, and having a respective center on, axis 74. The grooves are generically termed grooves 118. In she illustrated embodiment there are two grooves 118 separated by approximately 10 mm, with an upper groove being approximately 10 mm from disclike region 114, but other embodiments may have more than two grooves 118, and the spacing may be different from 10 mm.

As is described below an adapter 354 mates with adapter receiving section 58, and ribs 110 and grooves 118 ensure that when the adapter is inserted into the receiving section, the mating is positive. In positive mating there are countervailing forces on the adapter from at least one of the ribs and from at least one of the grooves that keep the adapter in a set position, so that frictional forces alone do not maintain the adapter in the position.

For adapter 54 grooves 118 enable a slap hammer to be used for extraction of pin 42. Grooves 118 may also be configured to provide positive mating for adapter 54, as for adapter 354.

It will be appreciated that pin 42 is a single piece, and that ribs 110 and grooves 118 enable the pin 42 to be adjusted and fixated radially and axially, with respect to axis of symmetry 74. Furthermore, grooves 118 may also be used for extraction of the pin.

Figure 3:
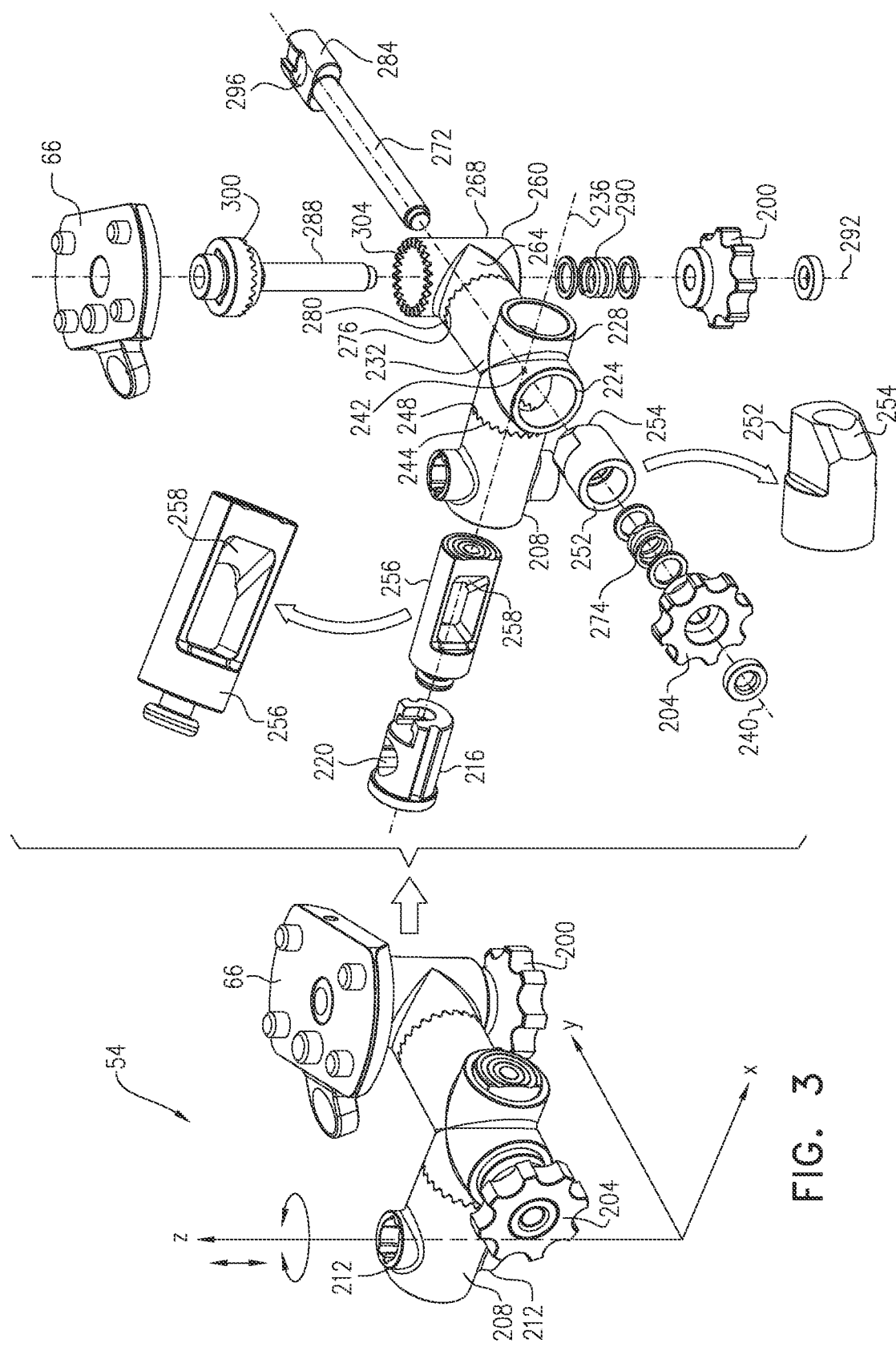
FIG. 3 is a schematic diagram of an adapter in an assembled and also in a partially exploded form, according to an embodiment of the present invention.

FIG. 3 is a schematic diagram of adapter 54 in an assembled and also in a partially exploded form, according to an embodiment of the present invention. Adapter 54 is configured to mate with proximal section 58 of pin 42, and is also configured to receive alignment target 62 on receiving base 66 of the adapter. Adapter 54 has multiple independent modes of motion, so having corresponding multiple independent degrees of freedom. In the disclosed embodiment adapter 54 has four different modes of rotation, and one mode of translation. The multiple modes of motion enable professional 22 to adjust the adapter, after it has been positioned on pin 42 and after target 62 has been attached to receiving base 66, so that the target is in a satisfactory position with respect to assembly 24 (FIG. 1). Once in position, professional 22 may lock the adapter in position using knobs 200 and 204.

Adapter 54 comprises a generally cylindrical pin holder 208 having a cylindrical symmetry axis. Pin holder 208 has two aligned approximately cylindrical protrusions 212, protruding orthogonally from opposite sides of the pin holder, that are configured to accept pin 42. For clarity the following description assumes that adapter 54 has been drawn on a set of orthogonal axes, where a z-axis corresponds to a symmetry axis of cylindrical protrusions 212, an x-axis is parallel to the symmetry axis of pin holder 208, and a y-axis is orthogonal to the x and z axes.

Protrusions 212 have internal projections that align with the surface of ribs 110, and that, when a pin grip 216 is translated parallel to the x-axis, are configured to mate with ribs of pin 42. Pin grip 216 is retained within holder 208 and comprises an opening 220, parallel to the z-axis, that accepts pin 42. Opening 220 is contoured so that in one direction of the translation of pin grip 216 it holds the pin, and in the reverse direction of the translation it releases the pin. The grip is configured, when knob 204 is rotated in a clockwise direction, to translate parallel to the x-axis so as to mate ribs 110 with the projections of protrusions 212. When ribs 110 are mated with the projections, holder 208, and thus adapter 54, cannot translate along the z-axis, so is locked with respect to this axis.

On the other hand, when knob 204 is rotated counterclockwise, adapter 54 may translate along the z-axis, i.e., is free to move with respect to the z-axis. In an alternative embodiment knob 204 also prevents rotation around the z-axis when rotated clockwise, and permits rotation when rotated counterclockwise. The possible rotations and translations are shown schematically in FIG. 3 by the double headed arrows proximate to the z-axis. Knob 204 thus acts as a lock for adapter 54, having a first locked position when turned clockwise wherein the adapter cannot move with respect to the z-axis, and a second unlocked position when turned counterclockwise wherein the adapter is able to move with respect to the z-axis. Knob 204 is herein also termed lock 204.

Adapter 54 further comprises a housing 224, having a first structure 228 intersecting with a second structure 232. The two structures are typically cylindrical and have respective cylindrical axes of symmetry 236, 240, and the housing is constructed so that the two axes of symmetry intersect orthogonally at an intersection point 242. Structures 228 and 232 of housing 224 intersect in the shape of a cross, and so the housing is also herein termed cross-piece 224. Pin holder 208 mates with first structure 228 of housing 224 by virtue of the fact that the two entities have mating sets of teeth—a set 244 for the pin holder and a set 248 for the first structure.

The operation of lock 204 in its locked and unlocked positions is described further below. Turning lock 204 between its locked and unlocked positions translates a wedge 252, resident in structure 224, along axis 240. Wedge 252 comprises a plane face 254 that is perpendicular to the xy plane and that makes an acute angle in an approximate range of 30°-60°, and typically approximately 45°, with the x-axis.

Wedge 252 in turn partially or fully engages a wedge receiver 256, resident in structure 228 and able to translate along axis 236. Wedge receiver 256 comprises a plane face 258, parallel to face 254 of wedge 252, and the two faces contact to provide the engagement described. Wedge receiver is coupled to pin grip 216.

When lock 204 is in its locked position, wedge 252 fully engages with wedge receiver 256 by translating towards intersection point 242, so that faces 258 and 254 have a maximum overlapping contact area. In the locked position, wedge receiver 256 pulls pin grip 216 towards intersection point 242, and the pin grip pushes on pin holder 208 so that teeth 244 and teeth 248 engage.

The movement of pin grip 216 towards intersection point 242 mates ribs 110 of pin 42 with the internal projections of protrusions 212, so locking the adapter with respect to the pin i.e., preventing translation along, and rotation around, the z-axis.

The engagement of teeth 244 with teeth 248 prevents pin holder 208 from rotating around axis 236.

Receiving base 66 is connected, as is explained in more detail below, to a receiving base holder 260. Base holder 260 consists of a first cylindrical structure 264 and a second cylindrical structure 268, the two structures intersecting in the shape of a "T" so that the leg of T corresponds to first structure 264 and the arms of the T correspond to structure 268. The two structures are hollow and structure 268 is also herein termed aperture 268. Base holder 260 is held in place in adapter 54 by a base holding rod 272, which at a proximal termination of the rod is threaded into lock 204, while a distal termination 284 of the rod end engages an internal wall of the holder. Teeth 280 are formed in a base of structure 264, and these teeth may engage with teeth 276 formed in a distal termination cylindrical structure 232.

Lock 204 has a female thread which engages a male thread of holding rod 272. Thus, when lock 204 is rotated clockwise into its locked position, in addition to the actions referred to above the lock translates holding rod 272 along axis 240 so that termination 284 pushes base holder 260 proximally, i.e., towards intersection point 242.

The translation also causes a spring 274 to compress, and teeth 276 and 280 to engage, so that holder 260 is locked in position, i.e., is not able to rotate around axis 240.

When lock 204 is rotated counterclockwise, into its unlocked position, the locking actions described above are reversed as is described hereinbelow.

Spring 274 decompresses, and rod 272 translates so that termination 284 moves distally, away from intersection point 242. Consequently, base holder 260 may be moved distally along axis 240 so that teeth 280 and teeth 276 disengage, so the holder may be freely rotated about axis 240.

Wedge 252 is able to translate proximally along axis 240, i.e., away from termination point 242. Consequently, pin holder 208 may be translated along axis 236, away from point 242, since wedge receiver 256 and wedge 252 are not forced into full engagement, but may partially engage. I.e., faces 258 and 254 no longer overlap to the contact area when lock 204 is in its locked position, but rather overlap with a lesser contact area. The pin holder translation disengages teeth 244 and teeth 248, so that the pin holder may be freely rotated about axis 236.

The disengagement also neutralizes the engagement of ribs 110 with the projections of protrusions 212. Consequently, when lock 204 is in its unlocked position, adapter 54 is able to translate along, the z-axis.

The description above describes how lock 204 locks and unlocks four movements adapter 54, the movements comprising translation and rotation with respect to the z-axis, rotation about axis 236, and rotation about axis 240. Embodiments of the invention comprise a further lock, knob 200, also herein termed lock 200, which is able to lock and unlock a fifth movement of adapter 54, as is described below.

Receiving base 66 is connected to an upper end of a supporting rod 288, and the rod aligns with an axis of symmetry 292 of aperture 268. A portion of rod 288 resides within aperture 268, and penetrates a circular opening 296 in termination 284. A lower end of rod 288 is threaded into lock 200.

A first set of teeth 300, symmetrical about axis 292, is formed at the upper end of rod 288 and teeth 300 are configured to mate with a second set of teeth 304 formed at an upper end of cylindrical structure 268.

Lock 200 has a female thread which engages a male thread in the lower part of rod 288. Thus, when lock 200 is rotated clockwise into its locked position, it compresses a spring 290 and lowers rod 288 along axis 292, so that teeth 300 and teeth 304 engage. The spring compression and teeth engagement lock rod 288, and thus receiving base 66 and attached target 62 or registration marker 71, with respect to adapter 54, so that the markers and the adapter cannot rotate about each other.

When lock 200 is rotated counterclockwise into its unlocked position, spring 290 decompresses, and rod 288 is raised along axis 292 so that teeth 300 and teeth 304 disengage. Once the teeth have disengaged, rod 288 and attached target 62 or registration marker 71 may be rotated freely about axis 292.

Figure 4A:
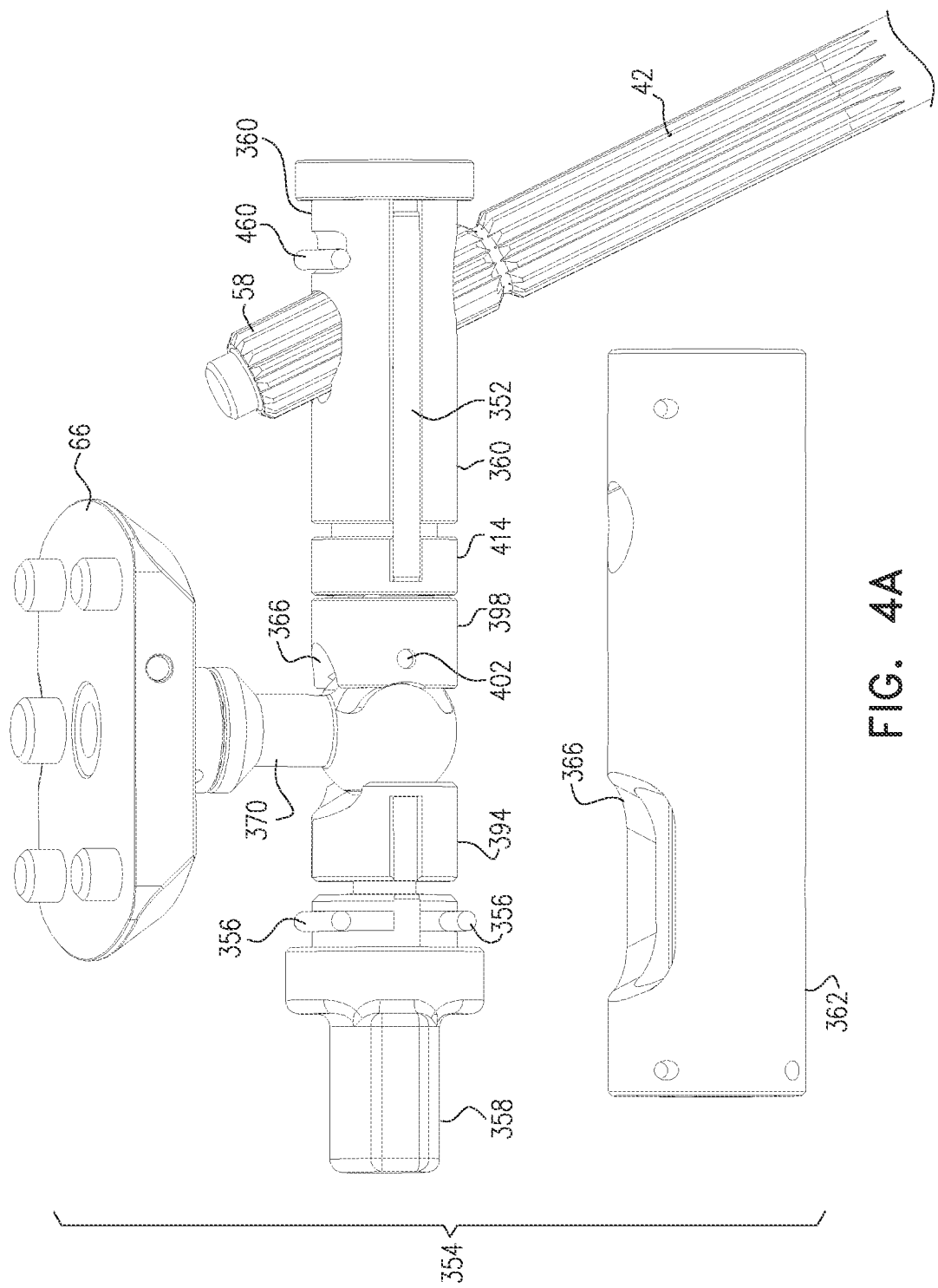
Figure 4B:
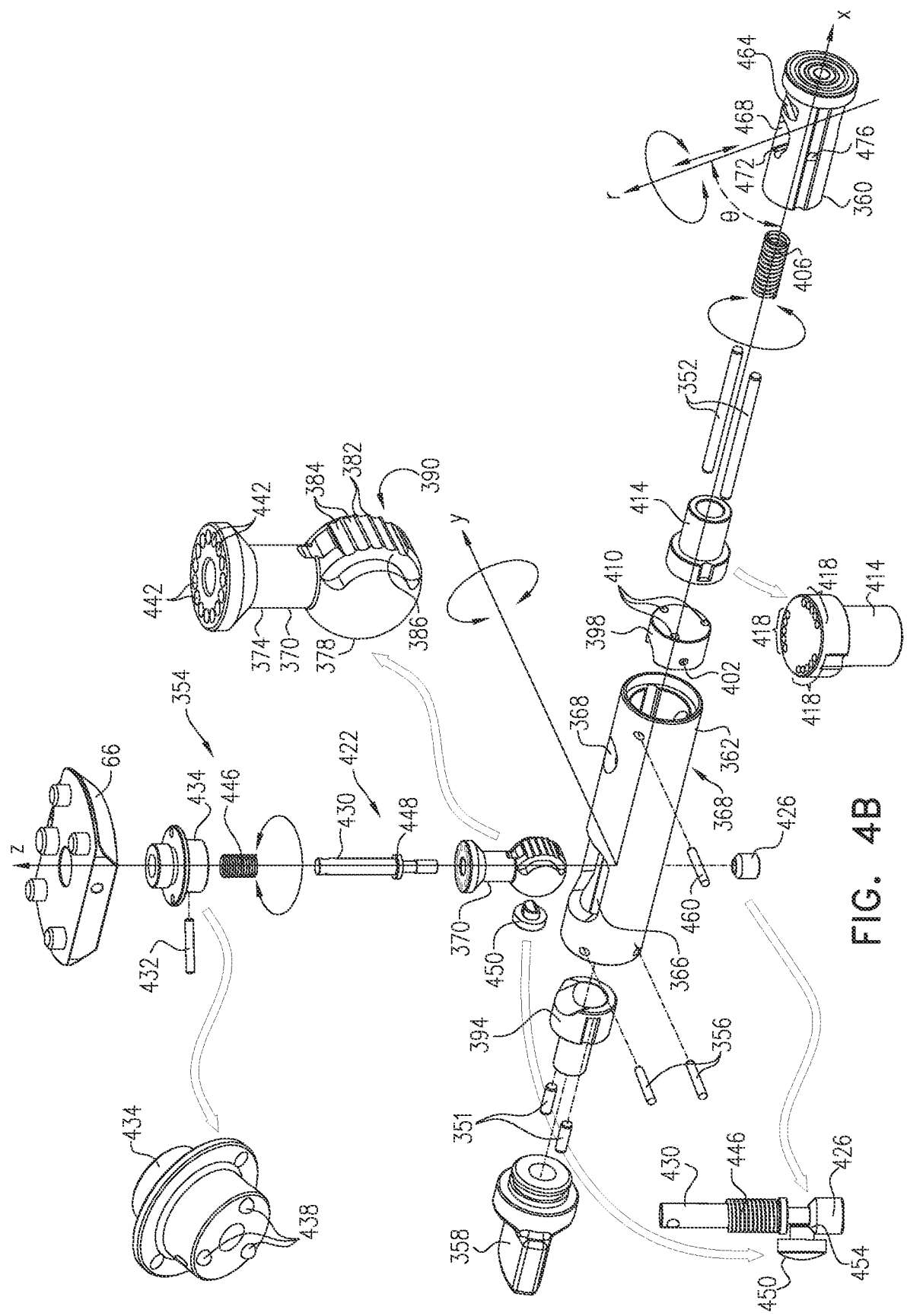
Figure 4D:
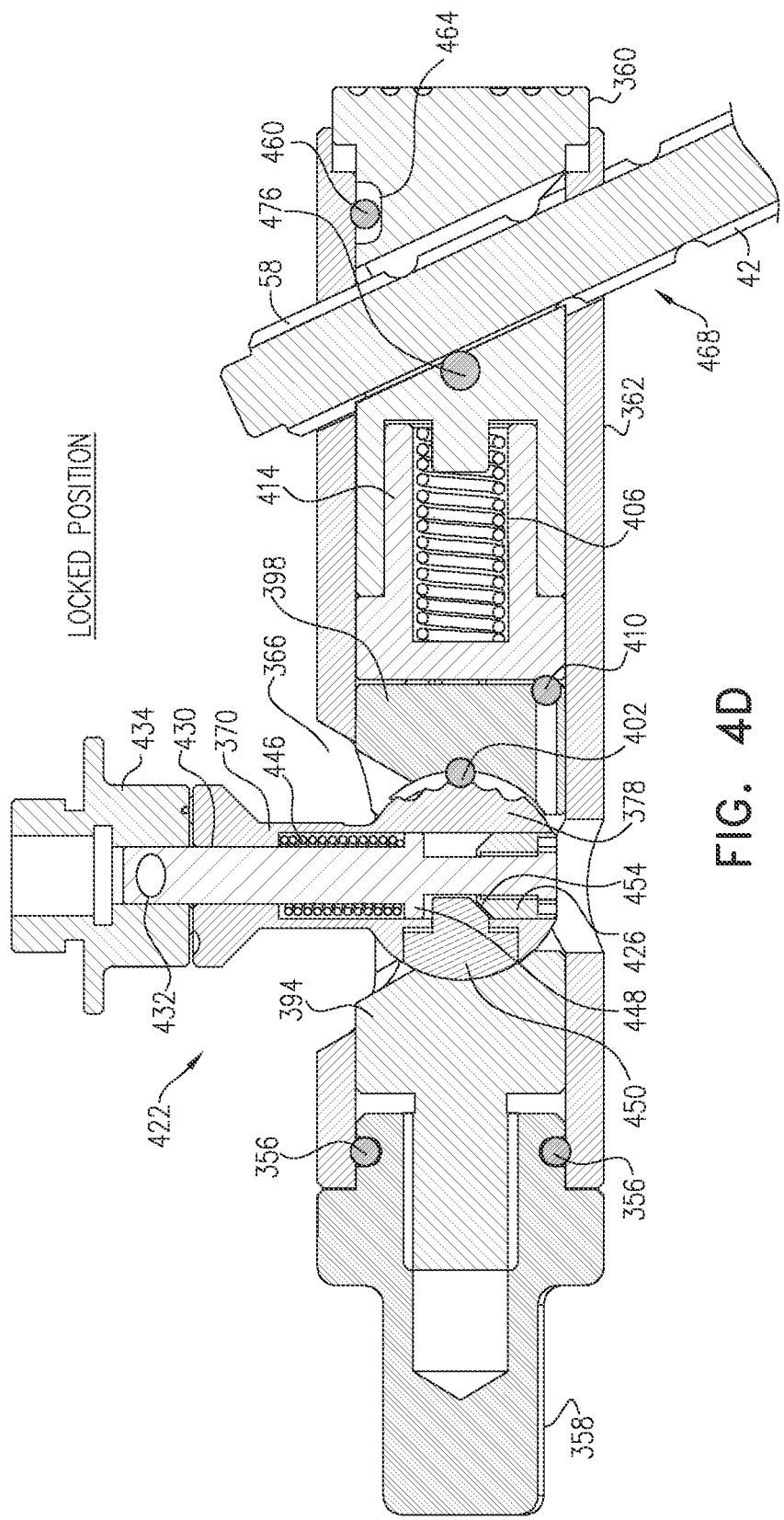

FIGS. 4A, 4B, 4C, and 4D are schematic diagrams of an adapter 354, according to an alternative embodiment of the present invention. FIG. 4A is a view of adapter 354 with a cylindrical housing 362 separated from other elements of the adapter. FIG. 4B is an exploded view of adapter 354. FIG. 4C is a cross-sectional view of adapter 354 when it is in an unlocked position, and FIG. 4D is a cross-sectional view of the adapter when it is in a locked position.

Apart from the differences described below, the operation of adapter 354 is generally similar to that of adapter 54 (FIGS. 1-3), and elements indicated by the same reference numerals in the description of both adapters 54 and 354 are generally similar in construction and in operation.

Referring to FIGS. 4A and 4B, as for adapter 54, adapter 354 is configured to mate with proximal section 58 of pin 42, and is also configured to receive alignment target 62 or registration marker 71 on receiving base 66 of the adapter. Adapter 354, like adapter 54, has multiple independent modes of motion, so having corresponding multiple independent degrees of freedom. In the disclosed embodiment adapter 354 has four different modes of rotation, and one mode of translation. The multiple modes of motion enable professional 22 to adjust adapter 354, after it has been positioned on pin 42 and after target 62 or registration marker 71 have been attached to receiving base 66, so that the target or the marker is in a satisfactory position with respect to assembly 24 (FIG. 1). Once in position, professional 22 may lock adapter 354 in position.

However, in contrast to adapter 54, which uses two locks 200 and 204 to lock the adapter in position, adapter 354 only uses one lock, a knob 358, also herein termed lock 358, to lock all five modes of motion of the adapter. I.e., knob 358 has two states: an unlocked state, where all of the five modes of motion are possible, and a locked state, where none of the five modes of motion are possible.

Adapter 354 comprises cylindrical housing 362, and in the description of the adapter the housing is assumed to define a set of xyz orthogonal axes wherein an x-axis corresponds to a symmetry axis of the housing. There is an approximately rectangular aperture 366 in the housing, and there is assumed to be a z-axis through the center of the aperture orthogonal to the x-axis. A y-axis is assumed to be orthogonal to the x and z axes. In the following description, proximal directions are assumed to be out of the paper, e.g., along the positive x-axis and along the negative y-axis, and distal directions are assumed to be into the paper, e.g., along the negative x-axis and along the positive y-axis.

Housing 362 is terminated at a distal end of the housing by lock 358, and at a proximal end of the housing by a pin retainer 360. Lock 358 is held to the distal end of the housing by pins 356 which permit the lock to rotate about the x-axis.

A receiving base mount 370, consisting a cylindrical section 374 fixedly attached to a spherical ball 378 is located within housing 362 so that a center of the spherical ball lies on the x-axis, and so that an axis of symmetry of the cylindrical section lies on the z-axis. Cylindrical section 374 protrudes from housing 362, through aperture 366. Mount 370 is coupled to receiving base 66, as is described below.

Ball 378 has formed on one side of its surface a set 382 of linear ridges, parallel to the y-axis, the set terminating in planes 386, 390 parallel to the xz plane. The ridges are typically separated by equal angles, as measured with respect to the center of the ball. In one embodiment there are six ridges distributed evenly with respect to the y-axis, separated by five linear valleys 384, and each of the valleys is separated by approximately 15°, but other numbers of ridges and other angular separations are possible.

Mount 370 is held in place within housing 362 by a first mount holder 394 and a second mount holder 398. First mount holder 394 is held in place by pins 351 which mate with internal grooves in housing 362. First mount holder 394 has, on its proximal side, a spherical surface that mates with the spherical surface of ball 378. Second mount holder 398 has, on its distal side, two planar mount retaining surfaces, parallel to the xz plane, that are configured to mate with surfaces 386 and 390, and that constrain the rotation of the mount holder as described below. In addition, second mount holder 398 retains a linear pin 402 that is parallel to the y-axis and that is configured to mate with any of linear valleys 384. Pin 402 also constrains the rotation of the mount holder, as is also described below.

Mount 370, the first and second mount holders, and pin 402 are held in place by a spring 406. In operation of adapter 354 spring 406 exerts a force on the mount, the mount holders, and linear pin 402, as well as on intervening elements within the housing that are described in more detail below. The force exerted by the spring depends on the position of lock 358.

Lock 358 has an internal female thread which mates with a male threaded portion of a distal end of first mount holder 394. In the unlocked position of the lock 358, illustrated in FIG. 4C, the lock is rotated to translate the first mount holder towards the lock. In the locked position of lock 358, illustrated in FIG. 4D, the lock is rotated so that the first mount holder translates away from the lock.

In the lock's unlocked position, spring 406 is compressed so that it exerts a first force, sufficient to maintain the elements within the housing in position, while permitting those designed to rotate to do so, as is described herein. In the lock's locked position, the spring is further compressed so that it exerts a second force greater than the first force. The second force is sufficient to prevent rotatable elements within the housing from rotating, so that they are locked in position.

Consequently, when lock 358 is in its unlocked position, mount 370 is free to rotate within its designed constraints I.e., surfaces 386 and 390 and the mating surfaces of mount holder 398 constrain mount 370 to rotate about the y-axis, in an xz plane. Furthermore, within this rotation, the mount may be maintained in any of the angles wherein pin 402 rests within a selected valley 384. Typically, in the unlocked position of the lock, professional 22 rotates mount 370 between valleys 384, hearing a click as pin 402 disengages and engages a valley, until the mount is in a satisfactory position. In one embodiment there is 15° between each of five valleys 384.

As is stated above, when lock 358 is in its locked position, mount 370 is locked in position, according to the valley 384 engaged by pin 402, so is not free to rotate from this position.

Second mount holder 398 (and thus mount 370) may also rotate about the x-axis, when lock 358 is in its unlocked position, and is prevented from such rotation when the lock is in its locked position, as is described below.

A plurality of substantially similar balls 410 are retained in a proximal side of the second mount holder, and are distributed symmetrically about the x-axis. In the illustrated embodiment and in the description below there are assumed to be three balls 410, but in other embodiments there may be more than three.

Second mount holder 398 and balls 410 are retained in contact with a cylindrically symmetrical mount holder retainer 414 by spring 406. Retainer 414 on its distal side comprises three sets of semispherical indentations 418, distributed symmetrically about, and equidistant from, the x-axis, and configured to mate with balls 410. On the proximal side of retainer 414 the retainer is held in alignment with pin retainer 360 by pins 352, the pins being retained by grooves within housing 362 and also permitting linear movement to retainer 414 and pin retainer 360. In the illustrated embodiment and in the description herein there are assumed to be five indentations 418 in each set, but other embodiments may have more or fewer than five indentations.

Thus, when lock 358 is in its unlocked position, second mount holder 398, and thus mount 370, may be rotated about the x-axis so that balls 410 align with and engage selected indentations 418, and it will be understood that there are five such stable alignments. In one embodiment the alignments are separated from each other by 15°.

When lock 358 is in its locked position, mount holder 398, and thus mount 370, is locked in position, according to the indentations 418 engaged by balls 410, so is not free to rotate from this position.

Independent of the rotations of mount 370 about the x and y axes as described above, receiving base 66 may rotate about the z-axis, when lock 358 is in its unlocked position, and is prevented from such rotation when the lock is in its locked position, as is described below.

Retained within mount 370, and aligned with the z-axis, is a cylindrically symmetrical receiving base support 422 comprised of a lower conical section 426, a central cylindrical section 430, and an upper disc-like section 434, the three sections being fixed together and having an axis of symmetry corresponding to the z-axis. Receiving base 66 is fixedly attached by a pin 432 to disc-like section 434.

A lower surface of section 434 comprises a plurality of indentations distributed symmetrically about and equidistantly from the z-axis, and the indentations retain respective balls 438. In the illustrated embodiment there are three indentations and three balls, but other embodiments may have more than three indentations and balls.

In an upper surface of mount 370 are formed a plurality of indentations 442 distributed symmetrically about the z-axis. The indentations are located at the same distance as balls 438 are from the axis. In the illustrated embodiment there are 15 indentations 442, separated by 24°, so as to encompass 360°, and so as to simultaneously receive balls 438. However, other embodiments may have fewer or more indentations 442, separated accordingly to encompass 360° and configured to simultaneously receive balls 438.

Once adapter 354 is assembled, balls 438 are maintained in contact with indentations 442 by a spring 446, retained within mount 370, that is configured to push down on a disc extension 448 of cylindrical section 430, and thus to push down disc-like section 434.

Support 422 is maintained in its position within mount 370 by a wedge element 450, which has a plane surface 454 that engages the conical surface of conical section 426.

When lock 358 is in its locked position first mount holder 394 is configured to push wedge element 450 proximally, so that plane surface 454 is a preselected distance from the z-axis, and so that the engagement of the plane surface with the conical surface is full. The full engagement translates support 422 down by a preselected distance along the z-axis, so that balls 438 are maintained in their respective indentations 442, and so that base 66 is locked in position.

When lock 358 is in its unlocked position first mount holder 394 does not push wedge element 450 proximally, so that plane surface 454 is at a greater distance from the z-axis than the locking preselected distance described above, and so that the engagement of plane surface 454 with the conical surface is partial. The partial engagement does not translate support 422 down by the preselected distance along the z-axis, so that balls 438 may be moved to other indentations 442, and so that base 66 may rotate freely about the z-axis.

The description above describes how receiving base 66 and adapter 354 have three independent modes of rotation, about the x, y and z axes, all of which may be locked by lock 358. The description below explains how lock 358 may also be used to lock and unlock adapter 354 with respect to pin 42.

Pin retainer 360 is held in position within housing 362 by spring 406, and also by a pin 460 that traverses a slot 464 in the retainer. Slot 464 is dimensioned to permit the retainer a small amount of proximal and distal motion, i.e., along the x-axis. Pin retainer 360 has formed in it an approximately cylindrical aperture 468 that is configured to accept and retain ribs 100 of pin 42. When pin retainer 360 is in housing 362, pin retainer aperture 468 aligns with apertures 368 in housing 362. When pin 42 is within aperture 468, axis 74 of the pin is assumed to lie on an r-axis of the aperture, the r-axis crossing the x-axis of adapter 354 at a pre-selected angle θ and lying in a pre-selected plane. In the illustrated embodiment θ is approximately 25° and the preselected plane is the xz plane. However, other embodiments may have other values of θ, including 90°, and the r-axis may lie in any plane that includes the x-axis.

Aperture 468 has formed on its distal side a rib engagement protrusion 472 that is parallel to the r-axis. In addition, a pin 416 is configured to penetrate pin retainer 360 diametrically, to cut protrusion 472, and to be parallel to the y-axis.

It will be understood that slot 464 permits pin retainer 360 to be pushed distally, i.e., into housing 362. Thus, when professional 22 pushes the pin retainer distally, the professional may insert ribs 100 of pin 42 into opening 468. Once inserted, the pin may be translated up and down along the r-axis, and may also be rotated around the r-axis. The translation and the rotation may be substantially completely free while the pin retainer is pushed distally.

When pin retainer 360 is not pushed distally, the force from spring 406 causes pin 476 to be able to engage grooves 118, and also causes protrusion 472 to engage ribs 100.

Spring 406 is configured, i.e., its size and spring constant are selected, so that when lock 358 is in its unlocked position, the engagement of grooves 118 and ribs 100 permits both translation of pin 42 along the r-axis and rotation around the r-axis. However, when lock 358 is in its locked position, spring 406 is configured to exert sufficient force to prevent disengagement of pin 476 from a retaining groove 118, and to prevent ribs 100 disengaging from protrusion 412.

In addition, the size and spring constant of spring 406 are such that when lock 358 is in its unlocked position, the rotations of mount 370 about the x and y axes, as described above, are permitted, and when the lock is in its locked position, the rotations are prevented.

It will be understood that in adapter 354 knob 358 acts as a single lock that locks all five modes of motion of the adapter. In addition, pin retainer 360, which together with knob 358 is within housing 362 so that the retainer and the knob are on a common axis, the x-axis of the housing, controls the motion of pin 42. Thus, as described above, pin retainer 360 may be pushed distally permitting pin 42 to rotate and translate freely, while when not pushed distally grooves 118 and ribs 100 may be engaged so as to prevent rotation and translation of the pin.

When knob 358 is in its unlocked state, all five degrees of freedom i.e., four rotations and one translation, are simultaneously possible, and each corresponding mode of motion may be adjusted independently and simultaneously without affecting the other modes.

When knob 358 is in its locked state, each of the five modes of motion may be locked in steps. In addition to the positive locking in steps, described above, the locking is typically assisted by friction between elements of adapter 354.

As stated above, pin 42 within aperture 468 lies on the r-axis which is at an angle θ to the x-axis, the axis of symmetry of adapter housing 362. Angle θ is typically selected to facilitate an anatomical procedure that uses pin 42

Figure 5:
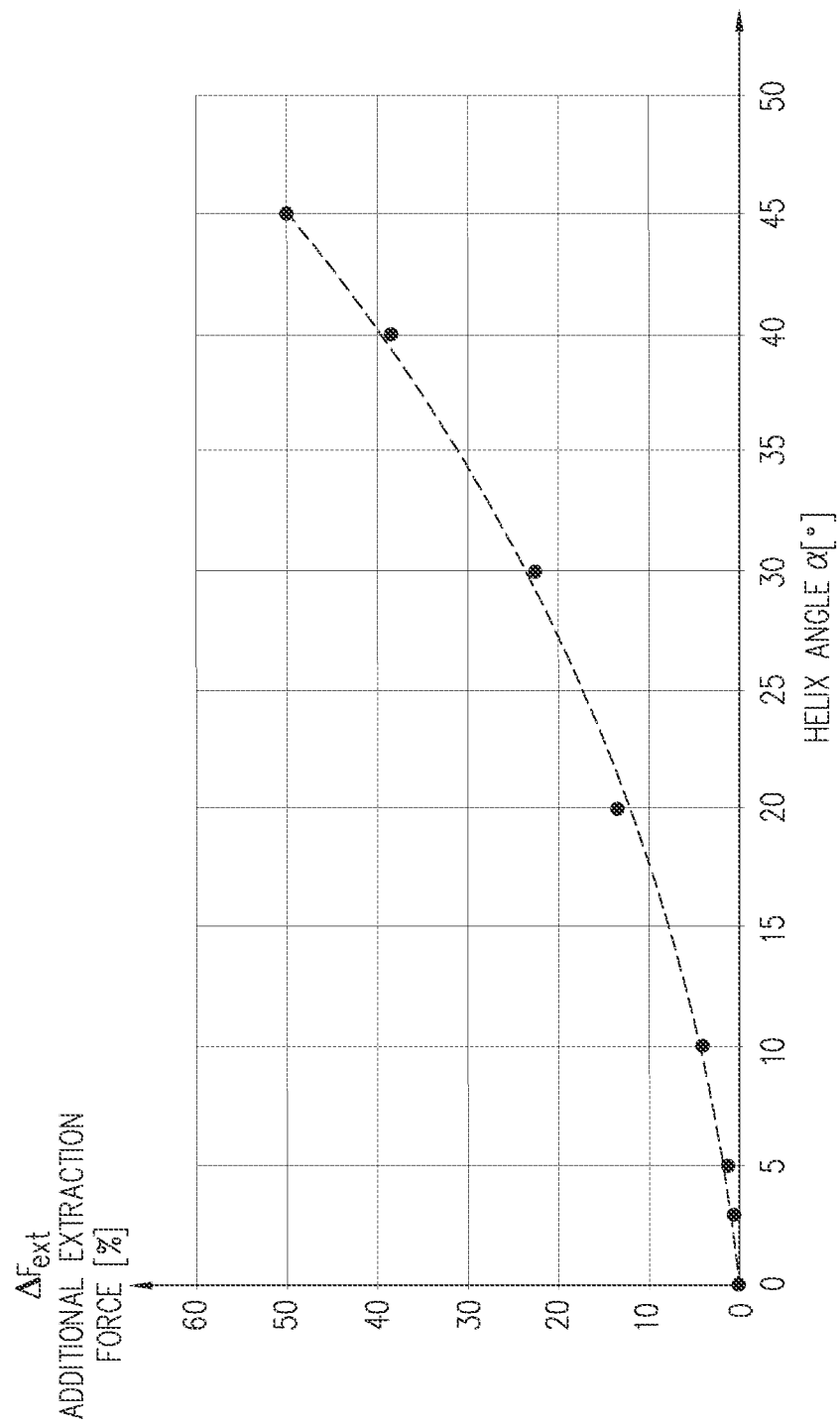
FIG. 5 is a schematic graph of an additional extraction force required for an iliac pin, vs. a helix angle of the pin, according to an embodiment of the present invention.

FIG. 5 is a schematic graph of an additional extraction force required for iliac pin 42 (FIGS. 2A-2D), vs. helix angle α of the pin, according to an embodiment of the present invention. Once pin 42 has been inserted into a patient's bone, it may be extracted providing a countervailing force is overcome. The countervailing force is a frictional force between the blades and the bone, and in embodiments of the present invention the frictional force is enhanced because of the non-zero helix angle α of blades 78. The enhancement to the frictional force, i.e., the increase in extraction force, $\Delta F_{ext}$, required, compared to the extraction force required for pins with straight blades, is comprised of two elements, a first element due to the increase on force on the blades due to the non-zero angle α, plus a second element due to the increased area of the blades also due to the angle α.

Thus, the increase in the extraction force $\Delta F_{ext}$ is given by equation (1):

$$\Delta F_{ext} = f(\alpha) \qquad (1)$$

where f(α) is a function of helix angle α

FIG. 5 is a schematic graph of $\Delta F_{ext}$ vs. α for an embodiment wherein pin 42 has an external diameter of 6 mm. The graph plots $\Delta F_{ext}$ as a percentage compared to the extraction force for a pin with straight blades. Those having ordinary skill in the art will be able to derive such graphs for pins of other diameters. The value of $\Delta F_{ext}$ is a metric of the increased stability of embodiments of the present invention, with pins having helical blades, compared to pins having straight blades. It will be appreciated from inspection of the graph that a preselected stability $\Delta F_{ext}$ may be achieved by producing the pin with a helix angle α given by the graph, and by an inverse of equation (1).

FIGS. 6A and 6B are schematic figures of mating teeth 244 and 248 implemented in adapter 54, according to an embodiment of the present invention. As described above, teeth 244 are formed in pin holder 208, and teeth 248 are formed in first structure 228 of housing 224. FIG. 6A illustrates the teeth when pin holder 208 rotates relative to first structure 228 so that the teeth are completely disengaged. FIG. 6B illustrates the teeth when the pin holder and first structure are rotated relative to each other so that the teeth are completely engaged.

Teeth 244 and teeth 248 are geometrically congruent to each other, and each tooth in the sets of teeth is in the general form of a wedge. In the following description teeth 244 are assumed to be comprised of wedges 644A, 644B, 644C, . . . , generically termed wedges 644, and teeth 248 are assumed to be comprised of wedges 648A, 648B, 648C, . . . , generically termed wedges 648. In the following description wedges 644A, 644B, 644C, . . . , and 648A, 648B, 648C, . . . , are also referred to as individual teeth 644A, 644B, 644C, . . . , and 648A, 648B, 648C, . . . .

Each wedge or tooth 644A, 644B, 644C, . . . , and 648A, 648B, 648C, . . . , is formed of two planes 644A1, 644A2; 644B1, 644B2; 644C1, 644C2, . . . , and 648A1, 648A2; 648B1, 648B2; 648C1, 648C2, . . . . The planes of any given wedge, for example planes 644B1 and 644B2 of wedge 644B, are oriented symmetrically with respect to the axis of symmetry of pin holder 208 and first structure 228, i.e., axis 236. Thus, each wedge, when projected orthogonally onto a plane comprising axis 236, appears as an isosceles triangle, since the two planes of the wedge are mirror images of each other and have substantially similar dimensions. In one embodiment an apex angle β of the isosceles triangle, illustrated schematically in FIG. 6B, is approximately 60°, but β may be larger or smaller than this.

The planes of a given tooth do not meet at a sharp line; rather the meeting region of the two planes, corresponding to the apex of the tooth, is curved or rounded, and the edges of the rounded sections are parallel to each other. In the figures, apices 644A3, 644B3, 644C3, . . . are the respective apices of Individual teeth 644A, 644B, 644C, . . . , and apices 648A3, 648B3, 648C3, . . . are the respective apices of individual teeth 648A, 648B, 648C, . . . . In addition, as shown in a callout 650 illustrating teeth 644B and 648B when disengaged, the edges of the two planes 644B1, 644B2, and 648B1, 648B2, are configured so that lines representing respective apices 644B3, 648B3 are not orthogonal to axis 236, but form a non-zero angle γ with a line orthogonal to the axis. In one embodiment γ is approximately 7°. Thus, in the completely disengaged state illustrated in FIG. 6A, meeting regions of teeth 244 and 248, for example, region 644B4 of tooth 644B and region 648B4 of tooth 648B are two approximately spherical surfaces that meet. Consequently, this is not an equilibrium position, so any possibility of a "dead position" for the mating teeth (at disengagement) is prevented. In addition, there is minimal wear when the surfaces do meet, thanks to the spherical and multispherical surfaces.

As stated above, apices 644A3, 644B3, 644C3, . . . and apices 648A3, 648B3, 648C3 of individual teeth are rounded. The planes of adjacent teeth are relieved at their meeting region. For example, planes 644A2 and 644B1, of teeth 644A and 644B meet at a relief region 644AB rather than meeting at a line. Other examples illustrated are relief regions 644BC of the meeting of teeth 644B and 644C, relief regions 648AB of the meeting of teeth 648A and 648B, and relief regions 648BC of the meeting of teeth 648B and 648C.

When teeth 244 and 248 are completely engaged, the symmetry of the teeth causes both planes of any given wedge of a tooth to contact both planes of mating teeth. For example, if in the completely engaged state tooth 644B lies between teeth 648A and 648B, plane 644B1 contacts plane 648A2, and plane 644B2 contacts plane 648B1. However, when completely engaged, the rounded apices of the teeth do not contact relief regions between the contacting teeth. For example, apex 644B3 of tooth 644B, aligns with relief region 648AB, but apex 644B3 does not contact any portion of teeth 648A and 648B.

The lack of contact in the engaged state is illustrated in a callout 66C, which shows rounded apex 648A3 of tooth 648A aligning with, but not contacting, relief region 644AB of teeth 644A and 644B. The rounded apex of each tooth, and the parallel edges of each apex, are illustrated in a callout 670 which is a perspective view of tooth 648A with apex 648A3.

It will be understood that because, in the completely engaged state, both planes of any given wedge are in contact with planes of mating teeth, there is no backlash in the completely engaged state.

It will be appreciated that in embodiments of the invention every single tooth has five inclined surfaces, and a rounded apex that has parallel edges as well as a spherical tip. In addition, at contact in the disengaged state, the two contacting spherical surfaces act to prevent a dead position occurring.

The above description applies to mating teeth 244 and 248. The description also applies, mutatis mutandis, to mating teeth 300 (on rod 288) with teeth 304 (on cylindrical structure 268), and to teeth 276 (on structure 232) mating with teeth 28C (on structure 264).

Figure 7:
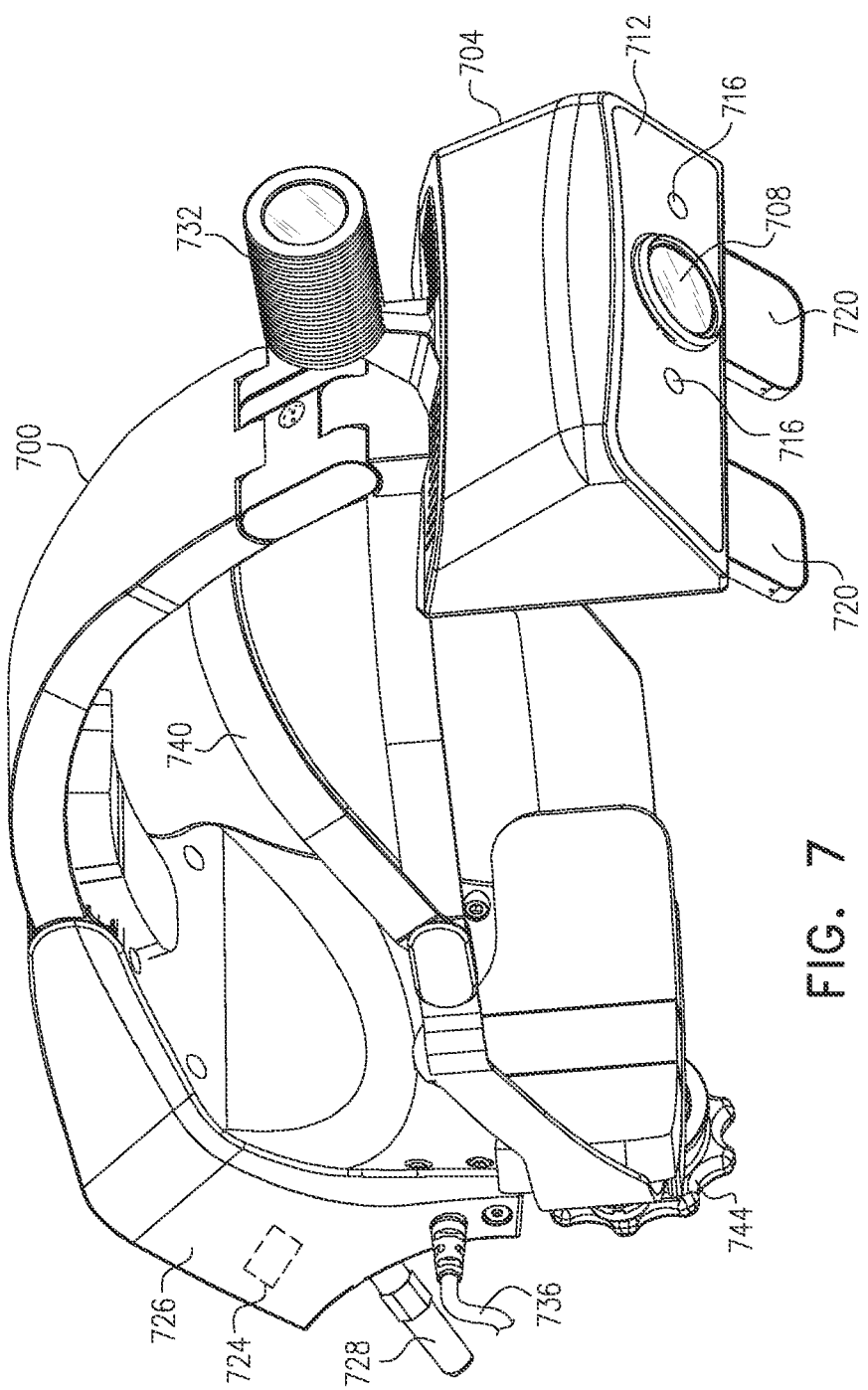
FIG. 7 is a schematic figure illustrating a head-up display (HUD), according to an embodiment of the present invention.

FIG. 7 is a schematic figure illustrating a head-up display (HUD) 700, according to an embodiment of the present invention. HUD 700 is worn by professional 22, and may be used in place of assembly 24 (FIG. 1). HUD 700 comprises an optics housing 704 which incorporates an infrared camera 708. Housing 704 also comprises an infrared transparent window 712, and within the housing, i.e., behind the window, are mounted one or more infrared projectors 716. Mounted on housing 704 are a pair of augmented reality displays 720, which allow professional 22 to view entities, such as part or all of patient 30 through the displays, and which are also configured to present to the professional images that may be received from database 38.

The HUD includes a processor 724, mounted in a processor housing 726, which operates elements of the HUD. Processor 724 typically communicates with processor 26 via an antenna 728, although in some embodiments processor 724 may perform some of the functions performed by processor 26, and in other embodiments may completely replace processor 26.

Mounted on the front of HUD 700 is a flashlight 732. The flashlight projects visibly spectrum light onto objects so that professional 22 is able to clearly see the objects through displays 720. Elements of the head-up display are typically powered by a battery (not shown in the figure) which supplies power to the elements via a battery cable input 736.

HUD 700 is held in place on the head of professional 22 by a head strap 740, and the professional may adjust the head strap by an adjustment knob 744.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus for mounting in a bone of a patient, comprising: a rigid elongated member having an axis of symmetry and a distal section, a proximal section, and an intermediate section connecting the distal and proximal sections; n helical blades, formed in the distal section, distributed symmetrically about the axis, each of the n helical blades having a helix angle greater than zero and less than 45°, and wherein a cross-section of the distal section, taken orthogonally to the axis of symmetry, comprises n mirror planes containing the axis of symmetry, wherein n is a whole number greater than one, wherein the n helical blades are configured to penetrate into the bone and engage stably therein; and a plurality of ribs, formed on an outer surface of the proximal section, each of the plurality of ribs being parallel to the axis of symmetry, wherein the proximal section further comprises one or more circular grooves positioned orthogonal to the axis of symmetry.

2. The apparatus according to claim 1, wherein the n helical blades taper by respective tapering planes to a common point at a distal tip of the distal section, so that the distal tip acts as a dilator.

3. The apparatus according to claim 1, wherein the n helical blades are configured to connect with the intermediate section in curved surfaces, so that the curved surfaces act as a support shoulder section when the n helical blades penetrate the bone.

4. The apparatus according to claim 1, wherein the n helical blades have n respective edges, and wherein the n respective edges are in the form of n cylindrical helices.

5. The apparatus according to claim 1, wherein the n helical blades have n respective edges, and wherein the n respective edges are in the form of n conical helices.

6. The apparatus according to claim 1, wherein the helix angle is configured so as to require a preselected force for extraction of the rigid elongated member when the n helical blades have penetrated into the bone, and wherein the preselected force is a metric of a stability of the rigid elongated member.

7. Apparatus for mounting in a bone of a patient, comprising: a rigid elongated member defining a central axis, the rigid elongated member having a distal section, a proximal section, and an intermediate section connecting the distal and proximal sections; n helical blades, formed in the distal section, distributed about the central axis, each of the n helical blades having an acute helix angle greater than zero and less than 45°, wherein n is a whole number greater than one, wherein the n helical blades are configured to penetrate into the bone and engage stably therein, and wherein the n helical blades taper by respective tapering planes to a common point at a distal tip of the distal section, so that the distal tip can act as a dilator; and a plurality of ribs, formed on an outer surface of the proximal section, each of the plurality of ribs being parallel to the central axis, wherein the proximal section further comprises one or more circular grooves positioned orthogonal to the central axis.

8. The apparatus according to claim 7, wherein the n helical blades are configured to connect with the intermediate section in surfaces that form wedges, so that the surfaces act to stabilize the rigid elongated member in position when the n helical blades have penetrated into the bone.

9. The apparatus according to claim 7, wherein the acute helix angle is configured so as to require a preselected force for extraction of the rigid elongated member when the n helical blades have penetrated into the bone, and wherein the preselected force is a metric of a stability of the rigid elongated member.

10. The apparatus according to claim 7, wherein a cross-section of the distal section, taken orthogonally to the central axis, comprises n mirror planes containing the central axis.

\* \* \* \* \*